(12) United States Patent
Iannarilli, Jr.

(10) Patent No.: US 6,678,632 B1
(45) Date of Patent: Jan. 13, 2004

(54) SPECTRO-POLARIMETRIC REMOTE SURFACE-ORIENTATION MEASUREMENT

(75) Inventor: Frank J. Iannarilli, Jr., Barrington, RI (US)

(73) Assignee: Aerodyne Research, Inc., Billerica, MA (US)

( * ) Notice: Subject to any disclaimer, the term of this patent is extended or adjusted under 35 U.S.C. 154(b) by 37 days.

(21) Appl. No.: 10/098,159

(22) Filed: Mar. 13, 2002

Related U.S. Application Data

(60) Provisional application No. 60/277,236, filed on Mar. 20, 2001.

(51) Int. Cl.[7] .............................................. G06F 15/00
(52) U.S. Cl. ...................................................... 702/153
(58) Field of Search ............................. 702/153, 159, 702/134, 152, 155, 167, 172; 280/341.3, 559.09

(56) References Cited

U.S. PATENT DOCUMENTS

| | | | | |
|---|---|---|---|---|
| 5,416,324 A | * | 5/1995 | Chun | 250/341.3 |
| 6,046,462 A | * | 4/2000 | Chun | 250/559.08 |
| 6,075,235 A | * | 6/2000 | Chun | 250/208.1 |

OTHER PUBLICATIONS

R. Windecker and H. J. Tizziani, Topometry of Technical and Biological Objects by Fringe Projection, Applied Optics, Jul. 1995, pp. 3644–3650, vol. 34, No. 19, Optical Society of America.

Klaus–Peter Proll et al., Application of a Liquid–Crystal Spatial Light Modulator for Brightness Adaptation in Microscopic Topmetry, Applied Optics, Dec. 2000, pp. 6430–6435, vol. 39, No. 34, Optical Society of America.

Lawrence B. Wolff et al., Constraining Object Features Using a Polarization Reflectance Model, IEEE Transactions on Pattern Analysis and Machine Intelligence, Jul. 1991, vol. 13, No. 7.

Frank J. Iannarilli, Jr. et al., Feature Selection for Multi–Class Discrimination via Mixed–Integer Liner Programming, Jan. 2002, pp. 1–16.

E. Joubert et al., 3–D Surface Reconstruction Using a Polarization State Analysis, J. Optics, Paris, 1995, pp. 2–8, vol. 26, No. 1.

Frank J. Ianarilli et al., Snapshot LWIR Hyperspectral Polarimetric Imager for Ocean Surface Sensing, Proceedings of SPIE, 2000, pp. 270–283, vol. 4133.

* cited by examiner

*Primary Examiner*—Michael Nghiem
(74) *Attorney, Agent, or Firm*—Cesari and McKenna, LLP

(57) ABSTRACT

To perform a monocular remote determination of a surface's three-dimensional orientation, an orientation-determination apparatus employs a radiation model in which the assumption is made that light incident upon the surface may be polarized but not elliptically. It makes polarimetric measurements of radiation received from the surface in each of a plurality of wavelength bands in the neighborhood of a known or inferable resonance in the surface's refractive-index spectrum. By employing the model, the apparatus matches the spectrum thus measured with the known behavior, in the neighborhood of a refractive-index resonance, of Fresnel-reflectance spectra as functions of incidence angle. Application-specific information is used to dispel minor ambiguities in the result.

20 Claims, 15 Drawing Sheets

DASHED: DoP = 20%
SOLID: DoP = 0

DASHED: DoP=20%
SOLID: DoP=0

θ = 30 DEGREES

θ = 70 DEGREES

SPECTRO-POLARIMETRIC REMOTE SURFACE-ORIENTATION MEASUREMENT

CROSS-REFERENCE TO RELATED APPLICATION

The present application claims the benefit of U.S. Provisional Patent Application Ser. No. 60/277,236, which was filed on Mar. 20, 2001, by Frank J. Iannarilli, Jr. et al. for Spectro-Polarimetric Remote Surface Orientation Measurement, and is hereby incorporated by reference.

STATEMENT REGARDING FEDERALLY FUNDED RESEARCH OR DEVELOPMENT

This invention was made with Government support under contract F19628-99-C-0040 awarded by the Air Force. The Government has certain rights in this invention.

BACKGROUND OF THE INVENTION

1. Field of the Invention

The present invention is directed to remote surface-orientation measurement. It is applicable particularly, but not exclusively, to passive, monocular systems for making such measurements.

2. Background Information

In the discussion that follows, the following bracketed codes will be used to refer to the sources identified next to them:

[Born&Wolf1965] *Principles of Optics*, M. Born and E. Wolf, Pergamon Press, (1965).
[Collett1993] *Polarized Light*, E. Collett, Marcel Dekker, (1993).
[Hapke1993] *Theory of Reflectance and Emittance Spectroscopy*, B. Hapke, Cambridge University Press, (1993).
[Iannarilli2000] "Snapshot LWIR hyperspectral polarimetric imager for ocean surface sensing", F. J. Iannarilli, J. A. Shaw, S. H. Jones, and H. E. Scott, *Proc. SPIE* Vol 4133 (2000).
[IannarilliRubin2002] "Feature selection for multi-class discrimination via mixed-integer linear programming, F. J. Iannarilli and P. A. Rubin, submitted (2002).
[Joubert1995] "3-D surface reconstruction using a polarization state analysis", E. Joubert, P. Miche, and R. Debrie, J. Optics 26, pp.2–8 (1995) (French journal; no longer published).
[Proll2000] "Application of a liquid crystal spatial light modulator for brightness adaptation in microscopic topometry", K. P. Proll, J. M. Nivet, Ch. Voland, and H. J. Tiziani, Applied Optics 39(34), 6430–35 (2000).
[Ward1994] *The Optical Constants of Bulk Materials and Films*, L. Ward, Institute of Physics Publishing, Philadelphia (1994).
[Windecker1995] "Topometry of technical and biological objects by fringe projection", R. Windecker and H. J. Tiziani, Applied Optics 34, 3644–3650 (1995).
[Wolff1991] "Constraining object features using a polarization reflectance model", L. B. Wolff and T. E. Boult, IEEE Trans. on Pattern Analysis and Machine Intelligence, 13(7), 635–657, (1991).
[Wooten1972] *Optical Properties of Solids*, F. Wooten, Academic Press, (1972).

There are numerous applications for non-contact acquisition of an object's three-dimensional surface geometry or topometry. Consequently, many types of topometric apparatus have become available, each offering relative strengths and realms of applicability. Optical approaches by nature offer the convenience and spatial resolution compatible with typically desired measurement scales. In 3D photography, retrieval of object topometry is attempted by using multiple viewpoints (stereometry), "shape-from-X" (where "X" can be shading, texture and other photometric attributes), or perhaps from illuminant time of flight by employing a synchronized light source and camera shutter. In the similar yet distinct "3D scanning" domain, object topometry can be retrieved by using two or more displaced cameras to triangulate a scanned laser-illuminated spot. Structured (incoherent) light or interferometric (coherent) retrieval techniques are also common.

These various approaches can be categorized in accordance with whether the measurement is based on the differential range to the subtended surface element, its stereometric disparity, or its orientation.

Differential range measurements by nature use a controlled (active, directed) illumination source. This category includes the structured light, interferometric, and "time-of-flight" techniques [Windecker1995]. Some of the practical challenges involve control of, or accounting for, spatial non-uniformity of illumination or surface reflectance [Proll2000]. An implicit requirement is the arrangement for pre-measurement setup, so the approach typically cannot be used spontaneously.

Stereometric-disparity approaches implicitly require that feature correspondence be ascertained. That is, they need to identify the point in the image taken from viewpoint A that represents the same real-world point as a given point in the image taken from viewpoint B. Active time-sequential spot illumination (e.g., by laser) overcomes the "matchpoint" ambiguity suffered by passive imaging, particularly when surfaces lack features. The effectiveness of spot illumination depends on whether enough light is scattered into the direction of the receiving sensor(s) (stationed at fixed viewpoint), so spot illumination works best for diffusely reflecting surfaces and not so well for glossy (quasi-specular) surfaces. Stereometric-disparity methods cannot be used for objects located outside the overlap in the tandem sensors' fields of view.

The photometric ("shape-from-X") measurements are by nature modulated by the object's surface orientation, which in turn modulates the observable reflectance and surface relief. A strong advantage that such methods (potentially) offer is monocularity, that is, the ability to employ a single sensor from a single viewpoint. This minimizes or eliminates the need for pre-measurement set-up. It thus enables these techniques to be used spontaneously over wide fields of regard. But shape-from-shading and shape-from-texture methods often suffer from ambiguities that typically confine them to ascertaining only relative (differential) rather than absolute surface orientation. One way to overcome the ambiguity is to employ variable-incidence active illumination, but this limits flexibility and measurement spontaneity.

Novel sub-categories of the photometric methods employ radiometric attributes beyond scalar intensity. Perhaps the most evident among these is polarimetry. For ideal smooth surfaces, the Fresnel equations relate the measurable polarimetric attributes, e.g., degree of polarization ("DoP") and angle of polarization ("AoP"), to surface orientation. This suggests the possibility of passive monocular 3D imaging, where the light sources are ambient illumination and/or thermal self-emission [Wolff1991, Iannarilli2000]. Specifically, the physics suggests a one-to-one mapping from polarimetric (DoP, AoP) to surface-orientation coordinates.

But closer investigation reveals that, without further refinement, such polarimetric imaging may itself be limited to ascertaining relative rather than absolute surface orientation. Now, by making a simplifying assumption, an approach described in [Joubert1995] does make a polarimetric determination of the surface orientation. But it relies on stereometric measurements (i.e., two or more independent measurements from different vantage points) to determine the angle that the line of sight makes with the surface normal. So far, there has been no reasonably robust way to determine three-dimensional surface orientation by passive polarimetry from a single vantage point.

One reason for this is that the degree of polarization for a given surface orientation can vary due to unknown surface roughness. Attributing the proper absolute scale to DoP is also confounded in thermal-infrared applications became the balance between surface self-emission (i.e., temperature) and reflected environmental illumination is unknown. For example, in an application of monochromatic infrared polarimetry to passive retrieval of ocean surface waveslope [Iannarilli2000], the radiometric balance between self-emission from the warm ocean and reflection from an either cold or warm sky varies the scale of DoP by a factor of 10.

To discuss the problem in more detail, we introduce the notation illustrated by FIG. 1, which is a diagram of the various planes and angles defined by a polarimetric sensor 28 and the surface 12 to be measured. The sensor may have imaging capability, in which case it resolves a point on surface 12 at viewing-angle coordinates ($\beta,\alpha$) with respect to its reference frame. We define a right-handed Cartesian sensor reference frame 14 such that the Z-axis is coincident with the sensor's optical axis. The Z-axis's positive direction is from the sensor's entrance aperture to its focal plane, i.e. along the direction of light propagation. If the sensor is non-imaging, the viewing-angle coordinates ($\beta,\alpha$) are merely (0,0) by definition.

Angle $\theta$ is the angle that the line of sight 16 forms with the measured surface 12's normal 18. Since the invention to be described below depends on a degree of specular reflection, $\theta$ will be referred to as the angle of incidence, and we will refer to the plane that the normal 18 forms with the line of sight 16 as the "surface plane of incidence." The line of sight and the Z axis together define another plane, which we will refer to as the "bending plane of incidence," and the angle between the surface and bending planes of incidence will be referred to as the rotation angle $\phi$. In rest of the discussion, we will refer to ($\theta,\phi$) as giving the surface's three-dimensional orientation because, once ($\theta,\phi$) is determined, the three-space vector $\hat{n}0$ normal to the measured surface can be obtained from the viewing-angle coordinates ($\beta,\alpha$) by, for instance, solving the system of equations (1):

$1\hat{o}\hat{s}$=Normalize[Cos $\alpha$ Sin $\beta$, Cos $\beta$ Sin $\alpha$, -Cos $\alpha$ Cos $\beta$]

SolveFor: $\hat{n}$ $\hat{n}\cdot 1\hat{o}\hat{s}$=-Cos $\theta$;

Normalize[$\hat{n}\times(-1\hat{o}\hat{s})$]·Normalize[$1\hat{o}\hat{s}\times[0, 0, 1]$]=Cos $\phi$;

Normalize[$\hat{n}\times(-1\hat{o}\hat{s})$]·Normalize[$(-1\hat{o}\hat{s})\times(1\hat{o}\hat{s}\times[0, 0, 1])$]=-Sin $\phi$;

$\hat{n}\cdot\hat{n}$=1; (1)

In Equation (1), the Normalize[ ] operation returns a vector of unit Euclidean length. The operators $\{\cdot,\times\}$ are respectively the dot (inner) and cross products. Although Equation (1) provides no closed-form solution, it can be solved by using standard numerical methods (e.g., least-squares Newton optimization).

We digress at this point to note that polarimetric radiance measurements of (incoherent, ergodic) electric-field orientation are by nature invariant to 180° coaxial rotation. This implies a 180° ambiguity in the polarimetrically inferred angle $\phi$: polarimetric approaches to orientation determination cannot by themselves indicate whether the surface normal points "up" or "down." But this is not a severe limitation, since application-specific considerations will often dispel this ambiguity. For example, one may know a priori that upward-oriented surfaces' brightnesses are greater than those of downward-oriented surfaces.

To understand the more-severe limitations of previous approaches to polarimetric orientation measurement, it helps to model how the surface under measurement modulates the observable Stokes spectral radiance. The Stokes vector, which is one way of expressing received radiation's polarization state, is defined as:

$I=I(0°, 0)+I(90°, 0)$, $Q=I(0°, 0)-I(90°, 0)$, $U=I(45°, 0)-I(135°, 0)$, $V=I(45°, 90°)-I(135°, 90°)$, (2)

where $I(\theta,\in)$ is the intensity of the light vibrations in the direction making an angle $\theta$ with the X-axis when the y-component is subjected to a retardation $\in$ with respect to the x-component. The literature also uses $[s_1,s_2,s_3,s_4]$ or $[s_0,s_1,s_2,s_3]$ to represent the Stokes parameters.

Equation (3) is a reasonably general model [Hapke1993] for the surface modulation of the measured Stokes radiance spectrum [Born&Wolf1965; Collett1993].

$$\begin{bmatrix} I_r \\ Q_r \\ U_r \\ V_r \end{bmatrix}_\lambda = \tau_\lambda \left( k_{\theta,\lambda} \begin{bmatrix} a_{\theta,\lambda} & b_{\theta,\lambda} & 0 & 0 \\ b_{\theta,\lambda} & a_{\theta,\lambda} & 0 & 0 \\ 0 & 0 & c_{\theta,\lambda} & d_{\theta,\lambda} \\ 0 & 0 & -d_{\theta,\lambda} & c_{\theta,\lambda} \end{bmatrix} \begin{bmatrix} I_i \\ Q_i \\ U_i \\ V_i \end{bmatrix}_\lambda + M_\lambda \begin{bmatrix} h_{\theta,\lambda} \\ 0 \\ 0 \\ 0 \end{bmatrix} + L_\lambda \begin{bmatrix} 1 - k_{\theta,\lambda}a_{\theta,\lambda} - h_\lambda \\ -k_{\theta,\lambda}b_{\theta,\lambda} \\ 0 \\ 0 \end{bmatrix} \right) + \begin{bmatrix} P_\lambda \\ 0 \\ 0 \\ 0 \end{bmatrix} \quad (3)$$

This equation shows that four right-hand-side additive terms contribute to the left-hand-side Stokes radiance. The first term is the quasi-specular Fresnel reflection of the illuminating Stokes radiance $[I_i, Q_i, U_i, V_i]_\lambda$, which is incident upon the surface from the Snell's-law direction, $-\theta$, and reflected to the sensor viewing the surface at the angle of incidence $\theta$. This first term includes an equivalent Mueller matrix for Fresnel reflection [Born&Wolf1965; Collett1993]. The scale factor $k_{\theta,\lambda}$ accounts for surface roughness and thus a diminution of the polarizance of an otherwise mirror-smooth surface material.

The second term is the quasi-diffuse reflection of the illuminating panoramic (hemispherical) radiance $M_\lambda$, presumed to be depolarized upon reflection and diffusely scattered in proportion to the surface's diffuse reflectance $h_{\theta,\lambda}$. In this model, the terms $k_{\theta,\lambda}$ and $h_{\theta,\lambda}$ are generally coupled, but this point is incidental to our purposes.

The third term is the thermal (Planck) emission; the black-body emission radiance $L_\lambda$ is vectorially scaled by the indicated Stokes components, which comply with Kirchhoff's Law. All of the first three terms represent radiation components that propagate from the object to the sensor and are thus scaled by the line-of-sight path transmittance $\tau_\lambda$. The fourth term is additive line-of-sight path radiance. To reduce notation, we assume non-polarized line-of-sight path radiance and transmittance.

The Fresnel-reflectance Mueller-matrix elements $a_{\theta,\lambda}$ and $b_{\theta,\lambda}$ are respectively the Fresnel average (power) reflectance and disparity, which are functions of optical wavelength $\lambda$ and angle of incidence $\theta$. The term "disparity" denotes the numerical difference in (power) reflectivity for electric-field polarizations perpendicular and parallel to the plane of incidence. The matrix elements $c_{\theta,\lambda}$ and $d_{\theta,\lambda}$ may be less physically familiar, but they nevertheless represent phase-coherent relationships between incident and reflected perpendicular and parallel polarized-radiance components.

Fresnel Reflectance Factors

Equation (4) presents equations for the Fresnel reflectance factors (as utilized in the Mueller matrix of Equation (3)) as a function of incidence angle $\theta$ and the surface's complex refractive index ($\eta,\kappa$):

$$n_\lambda = n_\lambda - i \cdot \kappa_\lambda \quad (4)$$

$$\rho_s = \frac{\cos[\theta] - \sqrt{\left(\frac{n_{surf}}{n_{med}}\right)^2 - \sin^2[\theta]}}{\cos[\theta] + \sqrt{\left(\frac{n_{surf}}{n_{med}}\right)^2 - \sin^2[\theta]}}$$

$$\rho_p = \frac{\sqrt{\left(\frac{n_{surf}}{n_{med}}\right)^2 - \sin^2[\theta]} - \left(\frac{n_{surf}}{n_{med}}\right)^2 \cos[\theta]}{\sqrt{\left(\frac{n_{surf}}{n_{med}}\right)^2 - \sin^2[\theta]} + \left(\frac{n_{surf}}{n_{med}}\right)^2 \cos[\theta]}$$

$$a_{\theta,n_\lambda} = \rho_s \cdot \rho_s^* + \rho_p \cdot \rho_p^*$$
$$b_{\theta,n_\lambda} = \rho_s \cdot \rho_s^* - \rho_p \cdot \rho_p^*$$
$$c_{\theta,n_\lambda} = \rho_s \cdot \rho_p^* + \rho_p \cdot \rho_s^*$$
$$d_{\theta,n_\lambda} = i(\rho_s \cdot \rho_p^* - \rho_p \cdot \rho_s^*)$$

Equation (4) employs complex-variable arithmetic, where $i=\sqrt{-1}$ and the superscript asterisk (*) denotes complex conjugate. It assumes that the sensor observes the surface of refractive index $n_{surf}$ though an intervening medium of refractive index $n_{med}$ [Born&Wolf1965]. In what follows, we assume that the intervening medium is air, whose refractive index is 1+0i, so $n_{med}$ drops out of Equation (4).

Defining $\phi$ and $\gamma$ by Relating the Surface-Plane-of-Incidence and Sensor Reference Frames It is important to realize that Equation (3) models the emanating Stokes radiance with respect to the surface plane of incidence. In this reference frame, the angle of polarization corresponding to any particular Stokes spectral sample is measured counter clockwise in FIG. 1 with respect to the plane of incidence's normal. However, the sensor measures the Stokes radiance with respect to its own coordinate frame. We define the apparent angle of polarization (appAoP) measurable by the Stokes analyzer in the sensor frame 24 as measured counter-clockwise in the X-Y plane with respect to the X-axis. Recall that the AoP is (conventionally) defined as Equation (5) indicates and is not to be confused with the so-called angle of the polarization ellipse:

$$AoP = \frac{1}{2} ArcTan[Q_r \cos\delta, U_r] \quad (5)$$

$$\delta = ArcTan\left[\frac{V_r}{U_r}\right]$$

The transformation from the surface plane of incidence to the sensor reference frame is modeled upon the behavior of a negligibly polarizing collimating optic (e.g., a refractive element operated in the regime of near-normal angles of incidence). It is highly likely that a polarimetric sensor will apply a collimated light beam through its Stokes analyzer.

For purposes of analysis, the collimating optic is envisioned as a virtual "bending surface" that redirects all rays from a given field angle direction ($\beta,\alpha$) into a ray bundle along the +Z-axis. This is the basis for using the "bending plane of incidence" nomenclature to refer to the plane defined by the line of sight and the Z-axis. It also makes apparent the "polarization ray tracing" that relates Stokes vectors across the reference-frame transformations involved. The result is that the AoP-to-appAoP transformation involves two coaxial Givens rotations. The first, $\phi$, is from the surface-plane-of-incidence frame into the bending-plane-of-incidence frame, and the second, $\gamma$, is from the latter frame into the sensor X-Y plane. In other words, two offset angles $\phi$ and $\gamma$ linearly relate AoP to appAoP:

$$appAoP - AoP = \gamma - \phi \quad (6)$$

As was mentioned above, rotation angle $\phi$ is measured counterclockwise from the surface plane of incidence's normal to that of the bending plane of incidence. Rotation angle $\gamma$ is measured clockwise to the X-axis from the bending plane of incidence's normal.

The known angles ($\beta,\alpha$) predetermine the line-of-sight vector and consequently the normal to the bending plane of incidence and thus the rotation angle $\gamma$. Equation (7) relates angle $\gamma$ to known ($\beta,\alpha$). Subscripted variables denote the reference-frame components (x or y) of the indicated vector variable.

$$\hat{los} = Normalize[\cos\alpha\sin\beta, \cos\beta\sin\alpha, -\cos\alpha\cos\beta] \quad (7)$$

$$\gamma = ArcTan\left[\frac{los_y}{\sqrt{los_x^2 + los_y^2}}, \frac{-los_x}{\sqrt{los_x^2 + los_y^2}}\right]$$

(This equation uses two arguments for the arctangent function ArcTan[x,y] to indicate that this is a "quadrant-aware" version of ArcTan[y/x]: it distinguishes first- and second-quadrant values from third- and fourth-quadrant ones.) The discussion below uses $\gamma$'s value to compute $\phi$.

Relating Stokes Vectors between the Surface Plane-of-Incidence and Sensor Reference Frames In the prior section, we established that a simple linear offset $\gamma-\phi$ relates the apparent angle of polarization (appAoP) measurable in the sensor frame to the AoP that would be measured in the surface plane of incidence. The equivalent Mueller-matrix transformation (Givens rotation) of the Stokes radiance from the surface plane of incidence into the sensor frame (denoted by primed quantities) is [Collett1993]:

$$\begin{bmatrix} I' \\ Q' \\ U' \\ V' \end{bmatrix} = \begin{bmatrix} 1 & 0 & 0 & 0 \\ 0 & \cos 2(\gamma-\phi) & \sin 2(\gamma-\phi) & 0 \\ 0 & -\sin 2(\gamma-\phi) & \cos 2(\gamma-\phi) & 0 \\ 0 & 0 & 0 & 1 \end{bmatrix} \begin{bmatrix} I \\ Q \\ U \\ V \end{bmatrix} = R(\gamma-\phi) \begin{bmatrix} I \\ Q \\ U \\ V \end{bmatrix} \quad (8)$$

Combining Equation (3) and Equation (8) yields an expression, Equation (9), for the Stokes radiance spectrum measured by the sensor:

$$\begin{bmatrix} I'_r \\ Q'_r \\ U'_r \\ V'_r \end{bmatrix}_\lambda = R(\gamma-\phi) \begin{bmatrix} \tau_\lambda \{k_{\theta,\lambda}(a_{\theta,\lambda}I_{i,\lambda}+b_{\theta,\lambda}Q_{i,\lambda})+h_{\theta,\lambda}M_\lambda+(1-k_{\theta,\lambda}a_{\theta,\lambda}-h_{\theta,\lambda})L_\lambda\}+P_\lambda \\ \tau_\lambda k_{\theta,\lambda}(b_{\theta,\lambda}I_{i,\lambda}+a_{\theta,\lambda}Q_{i,\lambda})-\tau_\lambda k_{\theta,\lambda}b_\lambda L_\lambda \\ \tau_\lambda k_{\theta,\lambda}(c_{\theta,\lambda}U_{i,\lambda}+d_{\theta,\lambda}V_{i,\lambda}) \\ \tau_\lambda k_{\theta,\lambda}(-d_{\theta,\lambda}U_{i,\lambda}+c_{\theta,\lambda}V_{i,\lambda}) \end{bmatrix} \quad (9)$$

$$\begin{bmatrix} I'_r \\ Q'_r \\ U'_r \\ V'_r \end{bmatrix}_\lambda = \begin{bmatrix} \tau_\lambda\{k_{\theta,\lambda}(a_{\theta,\lambda}(I_{i,\lambda}-L_\lambda)+b_{\theta,\lambda}Q_{i,\lambda})+h_{\theta,\lambda}M_\lambda+(1-h_{\theta,\lambda})L_\lambda\}+P_\lambda \\ \tau_\lambda k_{\theta,\lambda}\{(b_{\theta,\lambda}(I_{i,\lambda}-L_\lambda)+a_{\theta,\lambda}Q_{i,\lambda})\cos[2(\gamma-\phi)]+(c_{\theta,\lambda}U_{i,\lambda}+d_{\theta,\lambda}V_{i,\lambda})\sin[2(\gamma-\phi)]\} \\ \tau_\lambda k_{\theta,\lambda}\{(c_{\theta,\lambda}U_{i,\lambda}+d_{\theta,\lambda}V_{i,\lambda})\cos[2(\gamma-\phi)]-(b_{\theta,\lambda}(I_{i,\lambda}-L_\lambda)+a_{\theta,\lambda}Q_{i,\lambda})\sin[2(\gamma-\phi)]\} \\ \tau_\lambda k_{\theta,\lambda}(-d_{\theta,\lambda}U_{i,\lambda}+c_{\theta,\lambda}V_{i,\lambda}) \end{bmatrix}$$

Factors Confounding Inference of $(\theta,\phi)$ from the Stokes Radiance Spectrum Now, Equation (10) compares the number of known quantities in Equation (9) with its number of putatively unknown quantities, and the results make attempting such a computation appear ill-fated. Even if the surface's complex refractive index $n_\lambda$ and therefore Fresnel reflectance factors $a_{\theta,n_\lambda}$, $b_{\theta,n_\lambda}$, $c_{\theta,n_\lambda}$, $d_{\theta,n_\lambda}$ are known, the number of unknown terms still exceeds the knowns.

Knowns: $[I'_r, Q'_r, U'_r, V'_r]_\lambda, \gamma$

Unknowns:

→Orientation: $\theta,\phi$;

→Surface Parameters: $n_\lambda, k_{\theta,\lambda}, h_{74,\lambda}, L_\lambda$

→Illumination: $M_\lambda, [I_{i,\lambda}, Q_{i,\lambda}, U_{i,\lambda}, V_{i,\lambda}]$ →Propagation Path: $\tau_\lambda, P_\lambda$ (10)

Some workers in this art have simplified the problem by limiting it to conditions in which the surface is illuminated by only unpolarized light (i.e. zero-valued components $Q_{i,\lambda}$, $U_{i,\lambda}$, and $V_{i,\lambda}$). Under this assumption, Equation (9) simplifies to Equation (11).

$$\begin{bmatrix} I'_r \\ Q'_r \\ U'_r \\ V'_r \end{bmatrix}_\lambda = \begin{bmatrix} \tau_\lambda\{k_{\theta,\lambda}a_{\theta,n_\lambda}(I_{i,\lambda}-L_\lambda)+h_{\theta,\lambda}M_\lambda+(1-h_{\theta,\lambda})L_\lambda\}+P_\lambda \\ \tau_\lambda k_{\theta,\lambda}b_{\theta,n_\lambda}(I_{i,\lambda}-L_\lambda)\cos[2(\gamma-\phi)] \\ \tau_\lambda k_{\theta,\lambda}b_{\theta,n_\lambda}(I_{i,\lambda}-L_\lambda)\sin[2(\gamma-\phi)] \\ 0 \end{bmatrix} \quad (11)$$

From this, one can see that Equation (12) for angle $\phi$ immediately results from forming the ratio of measured $Q'_r$ and $U'_r$. (There is a 90-degree ambiguity in the inferred value of $\phi$, which is discussed later.)

$$\phi = \gamma \pm \frac{1}{2}\text{ArcCos}\left[\frac{\pm Q'_r}{\sqrt{Q'^2_r+U'^2_r}}\right] \quad (12)$$

$$\phi = \gamma \pm \frac{1}{2}\text{ArcTan}\left[\frac{U'_r}{Q'_r}\right]+\begin{Bmatrix} 0 \\ 90 \end{Bmatrix}$$

The Joubert approach mentioned above exploits this simplification to determine the rotation angle $\phi$, but it resorts to making two or more such $\phi$ measurements from different vantage points to derive $\theta$ geometrically.

From examination of Equation (11), one can appreciate how apparently intractable it is to infer angle $\theta$ radiometrically by taking measurements from only a single vantage point. Angle-$\theta$ retrieval appears confounded because surface roughness and line-of-sight transmittance (parameters $k_{\theta,\lambda}$ and $\tau_\lambda$), illumination $I_{i,\lambda}$, surface thermal emission $L_\lambda$, and refractive index $n_\lambda$ are unknown.

SUMMARY OF THE INVENTION

The present invention provides a way to make a polarimetric orientation determination in a way that is robust to these and other effects. According to the invention, the received radiation's polarization state is measured at several wavelengths in the neighborhood of a resonance in the target surface's refractive index. From these measurements, the surface's orientation is computed by taking advantage of an aspect of the relationship between reflected Stokes radiance and surface orientation.

Now, the fact that the Fresnel equations relate surface orientation to the reflected Stokes radiance is well known to those skilled in the art, as is the distinctive spectral behavior of the complex refractive index across a resonance feature. But I have recognized that this resonance behavior causes the Fresnel reflectance factors to have spectral patterns that change characteristically with angle of incidence. I have recognized further that, as manifested in the measurable Stokes radiance spectrum, these patterns are self-normalizable and thus invariant to nuisance parameters. I have also recognized that the inference problem can be simplified—without unduly circumscribing its range of applicability—by assuming that elliptical (but not necessarily linear) polarization is negligible in any surface-incident radiation whose reflection contributed to the received radiation.

According to the invention, therefore, the equations for the polarization state are solved for surface orientation by assuming (a) the absence of elliptical polarization in any incident radiation whose reflection contributed to the received radiation and (b) the dependence on angle of incidence that Fresnel reflectance exhibits as a function of wavelength in a refractive-index resonance's neighborhood. As will be seen below, this yields an orientation inference that is robust to most sources of nuisance variability and whose ambiguities can readily be dispelled by using application-specific information in many cases.

BRIEF DESCRIPTION OF THE DRAWINGS

The invention description below refers to the accompanying drawings, of which.

DETAILED DESCRIPTION OF AN ILLUSTRATIVE EMBODIMENT

Attempting Inference of $(\theta,\phi)$ from the Stokes Radiance Spectrum

Figure 2:
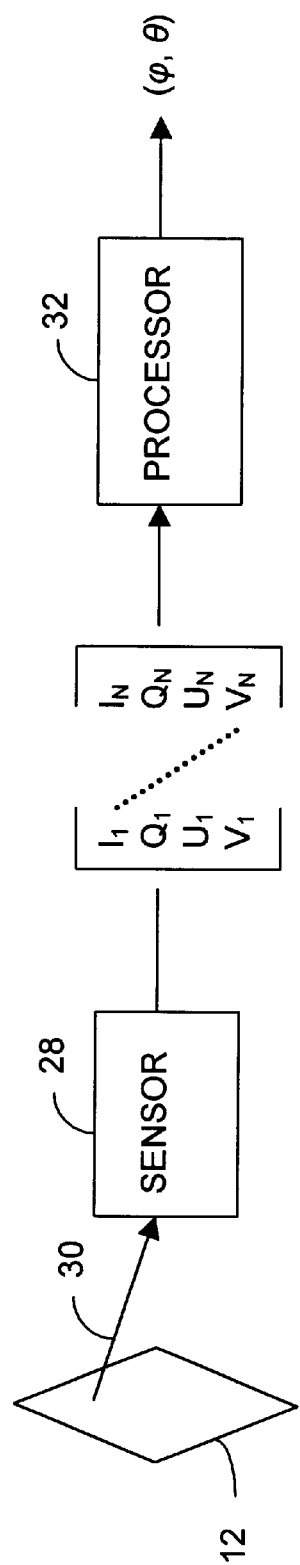
FIG. 2 is a block diagram of an apparatus used to implement the present invention's teachings.

FIG. 2 depicts a typical apparatus for practicing the invention and also indicates what the problem to be solved is. A spectro-polarimetric sensor 28 receives light 30 from a location on the surface 12 whose three-dimensional orientation is to be determined. The drawing depicts the sensor 28's output for a given location as a matrix consisting of a plurality of column vectors, one for each of a plurality of spectral channels, i.e., wavelength ranges. Together, the components of a vector associated with a given channel represent the polarization state of that channel's received light. For the sake of example, each column vector will be taken to be the components of the Stokes vector [Born&Wolf1965; Collett1993], although other polarization-state representations may be used instead in practicing the invention. Sensors for performing such polarimetric measurements are well known.

From the sensor's output, a processor 32 computes the surface 16's three-dimensional orientation and generates an output signal representative of that orientation. The drawing uses the notation $(\theta,\phi)$ to represent that orientation. As was observed above, though, some other orientation indication could be employed instead.

Figure 1:
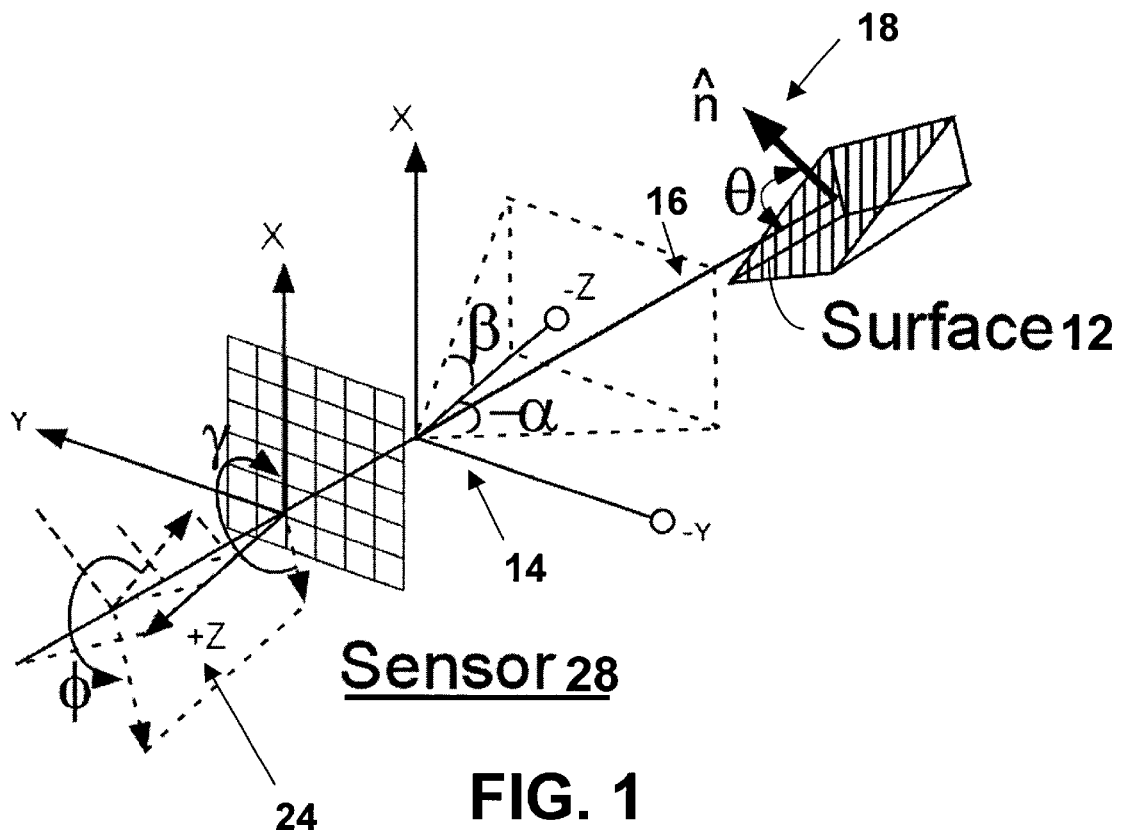
FIG. 1 is a diagram that depicts the planes of reference relevant to the present invention's orientation-inference techniques.
Figure 3:
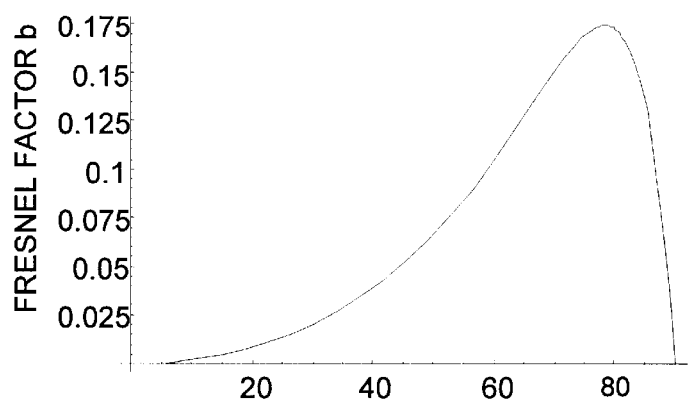
FIG. 3 is a plot of the Fresnel "disparity" reflectance factor as a function of incidence angle.

Attempting Inference of $(\theta,\phi)$ via Spectral Analysis of Stokes Radiance Spectrum In contrast with previous approaches, the present invention employs multiple spectral samples of the polarization state. Now, it is not immediately apparent that doing so would contribute much more than the noise reduction afforded by averaging multiple independent estimates of $(\theta,\phi)$. As was observed above, surface roughness and line-of-sight transmittance (Equation (10)'s parameters $k_{\theta,\lambda}$ and $\tau_\lambda$.), illumination $I_{i,\lambda}$, surface thermal emission $L_\lambda$, and refractive index $n_\lambda$ are unknown. If these were known, one could attempt to find the $\theta$ value that best fits the data, given the Fresnel equations (Equation (4)) relating the Fresnel reflectance factors, in this case matching against $b_{\theta,\lambda}$, to obtain the incidence angle $\theta$. But such matching would in general yield two possible and quite dissimilar values for angle $\theta$, given the one-to-two mapping between $b_{\theta,\lambda}$ and $\theta$ that FIG. 3 shows.

Alternatively, if the path radiance $P_\lambda$ is negligible in the case of zero thermal emission $L_\lambda$ (or instead zero illumination $I_{i,\lambda}$) and ideal surface glossiness (zero-valued surface diffuse reflectance $h_{\theta,\lambda}$, which also implies $k_{\theta,\lambda}=1$), one could form the ratio of measured $I'_r$ to $\sqrt{Q'^2_r+U'^2_r}$, which is the so-called Degree of (linear) Polarization (DoP). This equates to the ratio of Fresnel reflectance factors $a_{\theta,\lambda}$ and $b_{\theta,\lambda}$ (cf. Equation (11)), so the value of $\theta$ that yields the best-fitting ratio could be determined from the Fresnel equations. Again, though, the ratio of Fresnel reflectance factors $a_{\theta,\lambda}$ and $b_{\theta,\lambda}$ yields a humped function similar to FIG. 3's and thus the unfortunate one-to-two mapping (for a real-valued refractive index).

Nuisance variables are those unknown parameters that are of no particular application interest but nevertheless, because their values are unknown, interfere with the task of inferring the parameters of interest. The two methods mentioned above for radiometrically inferring angle $\theta$ apply to a domain that is vanishingly small compared with the possible space of unknown nuisance variability. Specifically, each presumes unpolarized illumination and requires either unavailable in-situ knowledge or idealized conditions (e.g., a mirror-smooth surface). To be practical, the radiometric inference of (θ,φ) must admit the broader domain of nuisance variability without assuming nuisance variables to be fixed at zero (e.g., unpolarized illumination) or idealized values. Unfortunately, as one may apprehend from Equations (9) and (10), such domain broadening disrupts the aforementioned methods for inferring angle θ and also prevents Equation (12) from serving as a way to obtain angle φ.

Two factors figure significantly in causing this problem. The first is that the intensity and polarization of surface-incident illumination is variable. An object having many differently oriented surfaces reflects into the sensor's line of sight illumination that reached the object from a range of panoramic angles. In general, this illumination's intensity and polarization both vary panoramically. This is particularly true for outdoor measurements in the visible band, which are characterized by strongly variable Rayleigh-scatter-induced skylight polarization. In the absence of a painstaking and typically impractical panoramic survey, the surface-incident intensity $I_{i,\lambda}$ is unknown, and its polarized components $Q_{i,\lambda}$ and $U_{i,\lambda}$ are possibly non-zero. Even for an ideal specular surface ($h_{\theta,\lambda}=0$), a non-zero $Q_{i,\lambda}$ and/or a non-zero $U_{i,\lambda}$ disrupts any straightforward DoP-to-θ relationship that might otherwise exist for an ideal surface with unpolarized illumination.

The second major problem-causing factor is that the balance between emission and reflection is ambiguous. Even if the surface is known to be ideally specular ($h_{\theta,\lambda}=0$) and the illumination is known to be unpolarized (zero-valued $Q_{i,\lambda}$ and $U_{i,\lambda}$), the inability to attribute the proper absolute scale to DoP (and thus to θ) in thermal-infrared applications prevents one from relying on a DoP-to-θ relationship. This inability results from the fact that the balance between surface self-emission (Planck term $L_\lambda$ regulated by unknown surface temperature) and incident environmental illumination $I_{i,\lambda}$ is not known. For example, in an application of monochromatic infrared polarimetry to passive retrieval of ocean-surface wave slope [Iannarilli2000], the radiometric balance between warm ocean (self-emission) and reflected sky radiance from either a cold or a warm sky varies the scale of DoP by a factor of 10.

Introducing multiple spectral samples does not seem to favorably alter the net balance between known and unknown variables. This is true even if, as the about-to-be-described illustrated embodiment does, we discard the conventional intensity measurement (Stokes component $I'_{r,\lambda}$), whose inclusion draws in more unknowns than knowns. Tallying the remaining knowns and unknowns and combining unknown factors into composite parameters where possible yield the summary that Equation (13) gives. That summary shows that the introduction of a spectral-measurement sample $\{Q'_r, U'_r, V'_r\}_\lambda$ (i.e. three knowns) unhelpfully draws in $k\{(I_{i,\lambda}-L_\lambda), Q_{i,\lambda}, U_{i,\lambda}, V_{i,\lambda}\}$ (i.e. four unknowns), thus more unknowns than knowns:

Knowns: $[-Q'_r, U'_r, V'_r]_\lambda, \gamma$

Unknowns:

→Orientation: θ,φ;

→Surface Parameters: $n_\lambda$

→Composite In-situ Parameters: $k_{\theta,\lambda} \cdot [(I_{i,\lambda}-L_\lambda) Q_{i,\lambda} U_{i,\lambda} V_{i,\lambda}]$ (13)

Robust Inference of (θ,φ) from the Stokes Radiance Spectrum

The present invention employs two key insights to infer surface orientation robustly despite these sources of unknown nuisance variability and non-ideality. The first is that few practical applications are lost—but a significant simplification is obtained—if, without assuming away all polarized illumination of the surface, any elliptical polarization incident upon the surface is assumed to be negligible; i.e., $V_{i,\lambda}$ is assumed to be 0. This simplifies Equation (9) to Equation (14):

$$\begin{bmatrix} I'_r \\ Q'_r \\ U'_r \\ V'_r \end{bmatrix}_\lambda = \begin{bmatrix} \tau_\lambda \{k_{\theta,\lambda}(a_{\theta,n_\lambda}(I_{i,\lambda}-L_\lambda) + b_{\theta,n_\lambda}Q_{i,\lambda}) + h_{\theta,\lambda}M_\lambda + (1-h_{\theta,\lambda})L_\lambda\} + P_\lambda \\ \tau_\lambda k_{\theta,\lambda} \{(b_{\theta,n_\lambda}(I_{i,\lambda}-L_\lambda) + a_{\theta,n_\lambda}Q_{i,\lambda})\cos[2(\gamma-\phi)] + c_{\theta,n_\lambda}U_{i,\lambda}\sin[2(\gamma-\phi)]\} \\ \tau_\lambda k_{\theta,\lambda} \{c_{\theta,n_\lambda}U_{i,\lambda}\cos[2(\gamma-\phi)] - (b_{\theta,n_\lambda}(I_{i,\lambda}-L_\lambda) + a_{\theta,n_\lambda}Q_{i,\lambda})\sin[2(\gamma-\phi)]\} \\ -\tau_\lambda k_{\theta,\lambda} d_{\theta,n_\lambda} U_{i,\lambda} \end{bmatrix} \quad (14)$$

The second insight is that significant additional information results if samples are taken in the neighborhood of a resonance in the surface's index of refraction. As will be explained below, particularly in connection with Equation (15), this yields expressions for the rotation angle φ that are remarkably independent of the nuisance variability terms. In fact, for the situation of non-zero polarized illumination, no solution (such as the one given below as Equation (15)) for angle φ is algebraically possible unless $V_{i,\lambda}$ is zero-valued and Fresnel reflectance factor $d_{\theta,\lambda}$ differs from zero to an extent that (for non-conductive materials) occurs only across resonances, i.e., only when the value of Equation (4)'s absorptance $\kappa_\lambda$ differs from zero significantly.

Additionally, taking samples in the resonance neighborhood means that the distinctive characteristics of the underlying resonance mechanisms are manifested in the Fresnel reflectance factors in the form of spectral patterns that change characteristically with the angle of incidence θ. The illustrated embodiment employs two such distinct manifestations of those patterns. The choice of which manifestation is used is determined by partitioning the inference domain into three specific "cases" (described in detail below).

Summary of Inference Regimes and Retrieval Error

As will be seen, the illustrated embodiment employs three alternative approaches to determining surface orientation from polarization-state measurements. Each approach measures the last three of the Stokes components but does not use the first one, $I'_r$, since that component's inclusion draws in more unknowns than knowns. That is, use of $I'_r$ draws in Equation (9)'s unknowns M, h, τ, and P.

Theoretically, the first of three approaches to be described below would suffice by itself, but practical limitations imposed by noise and finite measurement precision restrict certain approaches to respective regimes of applicability. The illustrated embodiment deals with this by dividing the problem into three inference regimes, called "Case 1," "Case 2," and "Case 3." Each regime is associated with a respective principal approach, but one or more of the other approaches may also apply in it.

All approaches assume that elliptically polarized surface-incident illumination is negligible. This assumption is justified in most practical applications. For such ellipticity to be non-negligible, the likely source of surface illumination would have to be a secondary glossy surface possessing a non-negligible imaginary refractive index (e.g. a metal, or a dielectric spectrally observed across one of its resonances) off which linearly polarized light is reflected.

Figure 4:
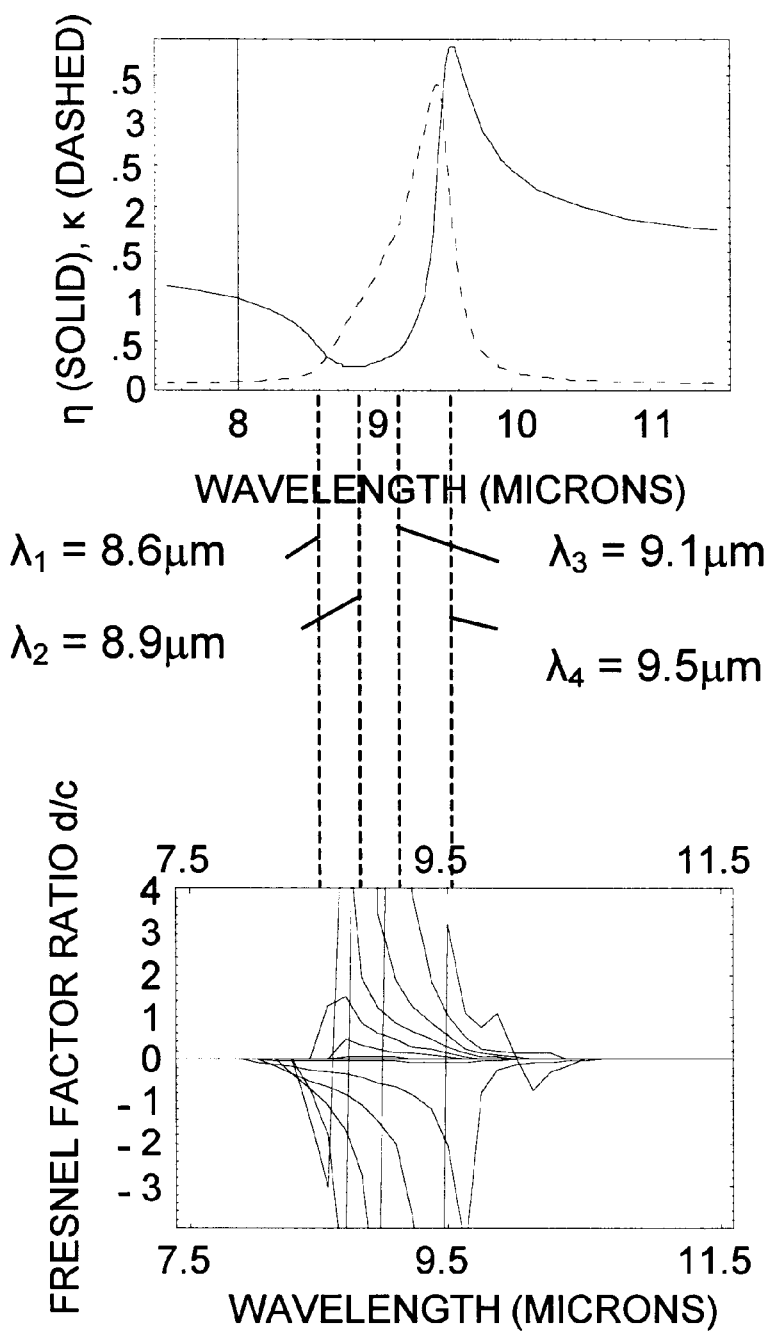
FIG. 4 is a diagram that plots both complex index of refraction as a function of wavelength and also, for various incidence angles, the ratio of the Fresnel reflectance factor c to the Fresnel reflectance factor d.

The method that applies to the Case 1 regime involves the joint inference of θ and φ. For "Case 1" inference, which is described in greater detail below, unique solutions to the joint inference of (θ,φ) are obtained by taking advantage of the fact that the spectral variation in the ratio of Fresnel reflectance factor $d_{\theta,\lambda}$ to Fresnel reflectance factor $c_{\theta,\lambda}$ is different for different values of θ when the spectral sampling occurs across a resonance feature. FIG. 4 illustrates this. That drawing plots that ratio for various incidence angles θ as a function of wavelength in the neighborhood of a resonance represented in that drawing by the refractive index's real and imaginary components. The range of applicability of the Case 1 method can be thought of as a region in the three-space that θ and the surface-incident radiation's DoP and AoP define. The inference regime for AoP between 90° and 180° is the mirror image of that for 0° to 90°. Since the Case 1 inference method retrieves θ and φ jointly, as we presently explain, the effectiveness regimes for θ and φ retrievals are the same. For small levels of unknown DoP, Case 1 retrievals are ineffective when θ is small. As DoP increases, Case 1 effectiveness extends to smaller values of θ and to values of unknown AoP closer to 0° or 90°.

Figure 5:
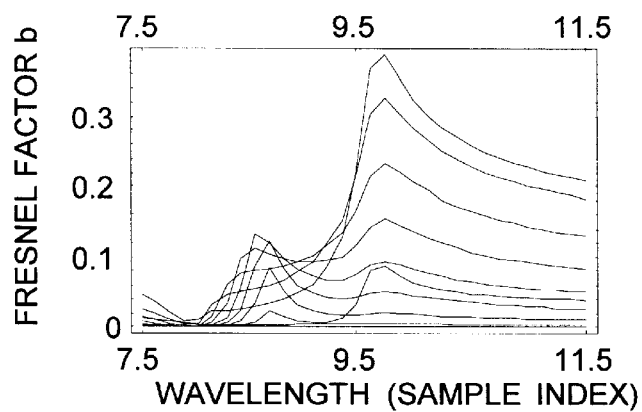
FIG. 5 is a diagram that plots the Fresnel "disparity" reflectance factor against wavelength for several incidence angles.

In the Case 2 regime, the below-described methods for retrieving θ and φ are separate. As will be seen, φ is calculated without relying on spectral behavior. Angle θ is directly inferred from the spectral behavior of the Fresnel reflectance factor $b_{\theta,\lambda}$ across a resonance. That factor exhibits a generic bimodal ("double-bump") feature, which FIG. 5 illustrates. I have recognized that the relative heights of these bumps change characteristically with the angle of incidence θ. Since it is these bumps' relative heights from which the illustrated embodiment infers the angle of incidence θ, this self-normalizing feature permits that angle's inference from the Stokes radiance spectrum to be invariant against most of the above-identified sources of nuisance variability. In particular, it is invariant against the surface roughness, path transmittance, and illumination intensity, including ambiguity in the balance between emission and reflection. For the smallest levels of DoP, the effective region for Case 2 retrieval of θ is complementary to Case 1. As DoP increases, neither Case 1 nor Case 2 is effective for small values of θ. Case 2 is effective for φ retrieval except for small levels of DoP when AoP is near 45° or 135°.

The method, described below, that is associated with Case 3 employs elements of the method associated with Cases 1 and 2 but is effective in a regime where those cases' methods are not.

We now turn to a more-detailed description of each method in turn.

Case 1: Inferring (θ,φ) for Obliquely Polarized Illumination ($U_{i,\lambda} \neq 0$)

The Case 1 approach is based on the assumption that the incident illumination's Stokes component $U_{i,\lambda}$ is non-zero. This assumption is not always valid, and whether it is valid in a particular case will rarely be known before the measurement is made. But the illustrated embodiment attempts to infer orientation by making this assumption and then tries another approach if the result is not satisfactory.

Under this assumption, the solution of Equation (14) for angle φ yields Equation (15), which is remarkably independent of unknown nuisance variability sources:

$$\phi = \gamma \pm \frac{1}{2} \text{ArcCos}\left[ \frac{-c_{\theta,\lambda} U'_r V'_r \pm \sqrt{d^2_{\theta,\lambda}(Q'^4_r + Q'^2_r U'^2_r) - c^2_{\theta,\lambda} Q'^2_r V'^2_r}}{d_{\theta,\lambda}(Q'^2_r + U'^2_r)} \right] \quad (15)$$

Equation (15) indicates that Equation (3)'s Fresnel reflectance factors $c_{74,\lambda}$ and $d_{\theta,\lambda}$ are still needed to solve for angle φ. This in turn implies knowledge of the complex-refractive-index spectrum for the surface under observation. Now, there are relatively few applications of the invention where this information is available before the measurement is made. For the sake of discussion, though, we will initially assume that it is available. As will later be shown, though, the fact that the measurements are taken in the spectral neighborhood of a resonance often makes that foreknowledge unnecessary; the constrained behavior of the Fresnel reflectance factors in a resonance neighborhood permits their inference from the spectral Stokes radiance measurements.

Figure 6:
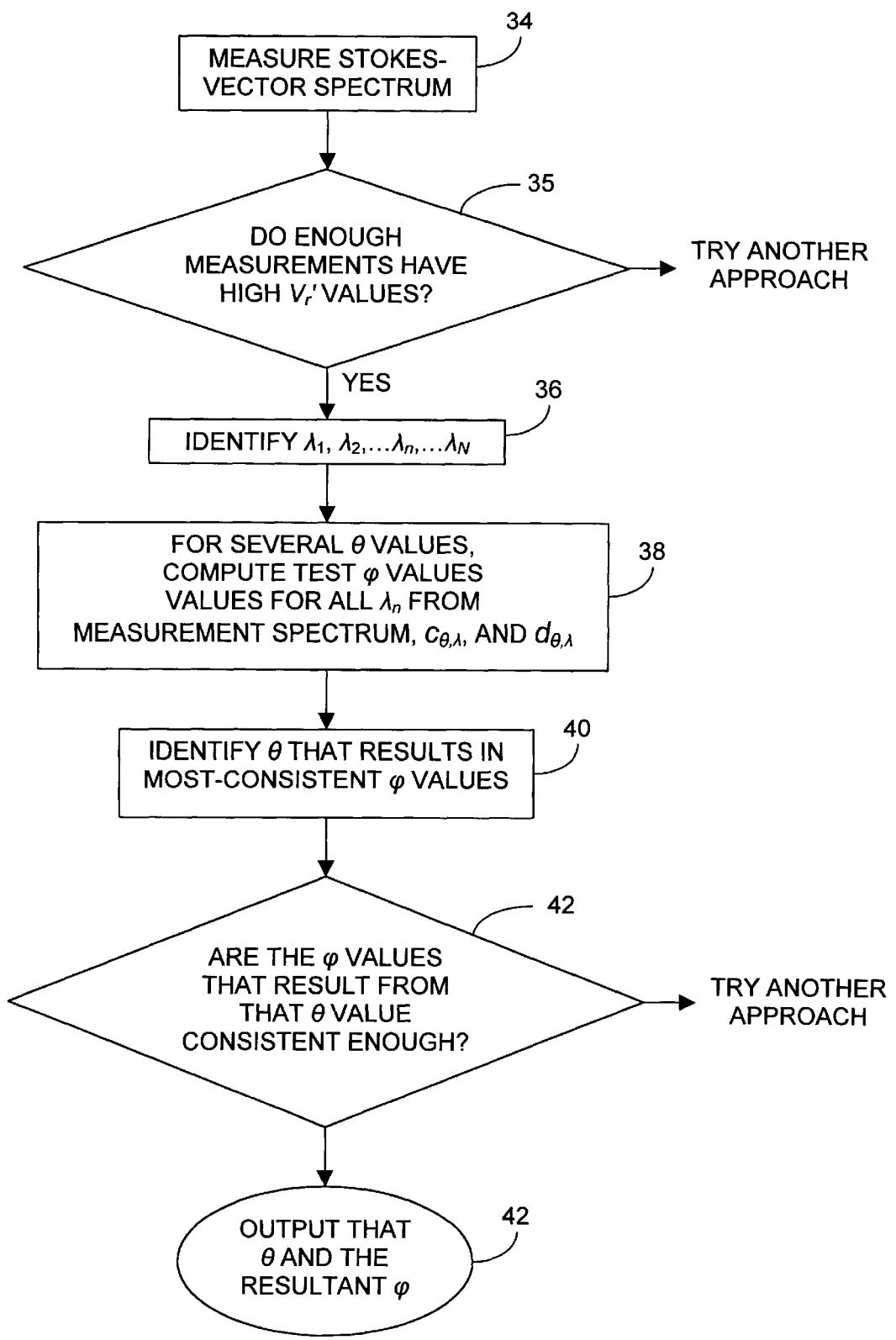
FIG. 6 is a flow chart depicting one of the techniques employed by the illustrated embodiment to infer a surface's orientation from spectro-polarimetric measurements of the light received from that surface.

FIG. 6 is a high-level flow chart of the Case 1 approach. First, the sensor makes the spectrum measurement that block 34 represents. As will be explained below, the technique of FIG. 6 is reliable only if the $V'_r$ values thus measured exceed the noise level by a great enough margin at enough wavelengths. As block 35 indicates, the processor next determines whether the measurements meet this criterion. If they do not, the processor employs the Case 2 technique described below instead of the technique of FIG. 6. Otherwise, it proceeds with the next step.

FIG. 6 depicts that as a step 36 in which the processor selects wavelengths within the neighborhood of an index-of-refraction resonance. Actually, those wavelengths will already have been chosen in some applications, because the type of surface material is sometimes known before the measurement begins. In other circumstances, the resonance-sampling wavelengths may need to be determined at measurement time (in a manner to be discussed below). And, in some such cases, an initial spectro-polarimetric measurement used to locate and identify a suitable resonance may need to be followed, after the wavelength determination, by follow-up measurements taken at wavelengths thereby determined to be best for sampling the resonance neighborhood properly.

In any event, the Stokes radiance samples measured at the selected wavelengths are used to compute trial solutions to Equation (14). Now, Equation (14) requires the incidence angle θ, which is not yet known. To compute the trial solution, therefore, the processor assumes a θ value and performs the computation of Equation (14) with the Stokes radiance samples $Q'_r$, $U'_r$, and $V'_r$ taken at that wavelength and with the Fresnel reflectance factors $c_{\theta,\lambda}$ and $d_{\theta,\lambda}$ values determined in accordance with Equation (4). As was mentioned above, we assume for the moment that prior knowledge of the surface material has given us the refractive-index spectrum that Equation (4) requires, although a later section discusses how to identify a resonance in an unknown material and determine the refractive-index spectrum, i.e., the values of (η,κ) as a function of wavelength λ, across the resonance. So enough information is available to compute φ at least formally from an assumed value of θ.

If that assumed θ value is correct (and the measurement falls within the Case 1 regime), then the φ values thereby computed for the various wavelengths will be consistent. To determine which θ value is correct, therefore, the processor repeats this computation for a number of different θ values, as block 38 indicates, and, as block 40 indicates, determines which one results in the most-consistent $\phi$ values. For each possible value of $\theta$, that is, the calculation involving Equation (15) employs the corresponding ($\theta$-dependent) Fresnel reflectance factors $c_{\theta,\lambda}$ and $d_{\theta,\lambda}$. The value of $\theta$ corresponding to the minimum obtained standard deviation of $\phi$ is taken to be the inferred angle of incidence.

Trial simulations of this inference technique were performed over a variety of assumed conditions (i.e., different values of surface-incident-illumination DoP and AoP, of surface-orientation angles $\theta$ and $\phi$, and of SNR). Each resulted in a distinct minimum in the plot of standard deviation of $\phi$ versus $\theta$, occurring at the correct values of assumed surface orientation. As expected, the minimum standard deviation of inferred $\phi$ decreases—and the sharpness of this minimum increases—with increasing SNR. The mean value of $\phi$ within the set corresponding to inferred $\theta$ is taken to be the inferred angle $\phi$. The corresponding standard deviation is indicative of the confidence interval, or, similarly, the "noise-equivalent differential $\phi$" ("NEd$\phi$"). As blocks 42 and 44 indicate, the inferred $\theta$ and $\phi$ values thereby identified are taken as the correct orientation if the NEd$\phi$ is low enough.

If none of the assumed $\theta$ values yields a low enough NEd$\phi$, on the other hand, then the measurement presumably did not fall within the Case 1 regime, and some other approach needs to be taken. Before we discuss the other approaches, though, we will discuss some implementation subtleties in the Case 1 approach and explain its underlying foundation, optimizations, performance, and regime of applicability.

There are three implementation subtleties that the illustrated embodiment employs in performing the inference technique just described. The first pertains to the possible generation of complex arguments of the ArcCos[ ] function in Equation (15). This can occur for some combinations of trial $\theta$ value and spectral-sample location $\lambda$. The illustrated embodiment simply excludes such combinations when they occur.

Figure 7:
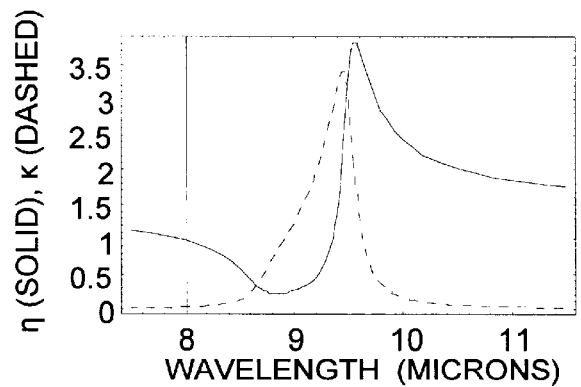
FIG. 7 is a plot depicting the spectral behavior of a surface's refractive index across a Lorentzian resonance.
Figure 8:
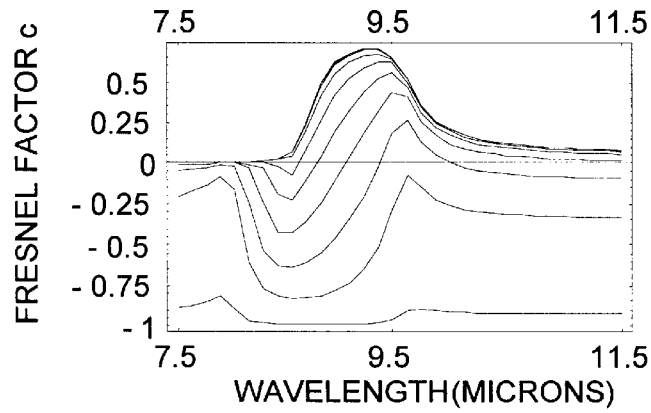
FIG. 8 is a diagram that plots, for several angles of incidence, the Fresnel reflectance factor c as a function of wavelength across a Lorentzian resonance.
Figure 9:
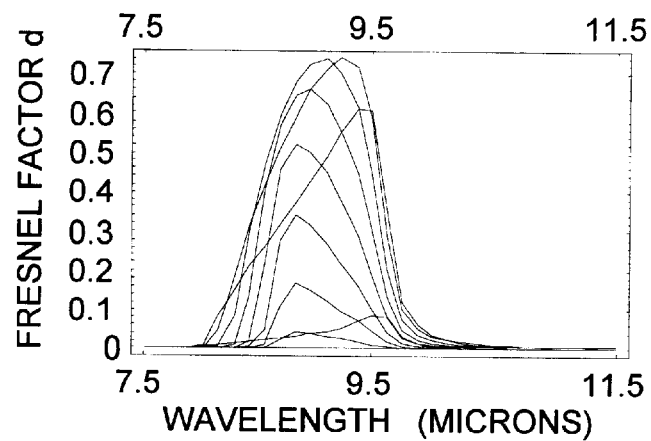
FIG. 9 is a diagram that plots, for several angles of incidence, the Fresnel reflectance factor d as a function of wavelength across a Lorentzian resonance.

The second subtlety pertains to SNR. Equation (15) yields undefined values for $\phi$ if the Fresnel reflectance factor $d_{\theta,\lambda}$ is near zero. FIGS. 7, 8, and 9 together illustrate the behavior, in the neighborhood of a resonance, of the (complex) index of refraction and, for various $\theta$ values, of Fresnel reflectance factors $c_{\theta,\lambda}$ and $d_{\theta,\lambda}$. FIG. 9, which depicts $d_{\theta,\lambda}$'s behavior, indicates that $d_{\theta,\lambda}$ is near zero away from the center of an absorption (resonance) peak. Equation (15) is valid only for non-zero $U_{i,\lambda}$ (surface-incident Stokes-radiance component); if $U_{i,\lambda}$ is zero, Equation (15) reduces to Case 2, which is discussed below. Equation (9) indicates that the measured Stokes radiance component $V'_r$ will be near zero if either $d_{\theta,\lambda}$ or $U_{i,\lambda}$ is near zero. As FIG. 6's block 35 indicates, therefore, near-zero values of measured $V'_r$ "flag" Stokes-radiance spectral samples that should be excluded from the Case 1 technique. "Near zero" is defined below. Simulations of the technique yielded accurate results only when $V'_r$'s was large enough with respect to the noise level. An SNR of 4:1 proved to be a satisfactory exclusion threshold for $V'_r$.

The third subtlety pertains to the ambiguity in the sign in front of Equation (15)'s radical. For each particular assumed value of $\theta$, this sign ambiguity is resolved by minimizing the variance of the set of $\phi$ values that the Equation (15) computation yields. One could exhaustively evaluate $\phi$-value sets for all possible combinations of signs (substituting + or − in Equation (15) for each spectral sample in the set). This imposes computational complexity order $O[2^N]$, where N is number of samples in set. This can be reduced to order $O[N^2]$, though, by recognizing, on the basis of observed simulation results, that notionally stepping across a sample set ordered by wavelength can result in the sign's being flipped at most twice and thus in at most three spectrally contiguous blocks of same-signed sample evaluations in Equation (15). The illustrated embodiment finds the minimum-variance set by exhaustive evaluation over all such permissible sign-flip sequences. It also imposes a minimum requirement of four spectral samples to form a sufficient ensemble for $\phi$ variance estimation.

Joint Inference of $(\theta,\phi)$: 90-degree Ambiguity in $\phi$

The sign ambiguity in front of the ArcCos[ ] term in Equation (15) is responsible for an ambiguity in $\phi$'s value. One might resolve this ambiguity by first back-substituting the inferred $\theta$ and, sequentially, the inferred $\phi=\gamma-$ArcCos[ ]/2, then $\phi=\gamma+$ArcCos[ ]/2 into Equation (14), solving for the three unknown surface-incident terms $\{k(I_{i,\lambda}-L_{i,\lambda}), kQ_{i,\lambda}, kU_{i,\lambda}\}$. The ambiguity is then potentially resolved by choosing whichever $\phi$ value yields the set of unknown surface-incident terms most consistent with application-specific knowledge of their relative values.

Joint Inference of $(\theta,\phi)$: Underlying Foundation and Optimization

The above-described method for joint inference of $(\theta,\phi)$ is based upon detecting consistency in a set of inferred $\phi[\lambda]$ samples taken at a plurality of sample spectral locations $\lambda$. But measuring and processing each sample takes time, and time may be at a premium in some applications. In those applications, it will be preferable to reduce the number of samples to the minimum that affords the needed accuracy. The choice of the optimal set and number of features is the "feature selection" problem. Although many feature-selection methods are available, the chosen method should handle multiple classes and maximize interclass margins as a principal criterion [IannarilliRubin2002]. Among the factors to be considered in the selection process is that the solution of Equation (15) is invariant to any scale factor common to the Fresnel reflectance factors $c_{\theta,\lambda}$ and $d_{\theta,\lambda}$. So a necessary condition for choosing the two or more spectral samples is that the ratio of $d_{\theta,\lambda}$ to $c_{\theta,\lambda}$ must differ between them. A further necessary condition is that the spectral variation of this ratio differs among various values of $\theta$. The present invention exploits my finding that these conditions can indeed be satisfied if the samples are taken in the neighborhood of a refractive-index resonance.

Whether these two conditions, which are necessary, are also sufficient depends on the phase-space structure of Equation (15). Unfortunately, since Equation (15) is highly non-linear, standard determinations of singularities and intrinsic dimensionality, applicable to linear equations, cannot be applied. Instead, I have found that these necessary conditions can be met by appropriate spectral-sample selection adapted to the particular resonance feature at hand, and I have empirically demonstrated their sufficiency by obtaining unique and correct inferences for $(\theta,\phi)$.

Figure 10:
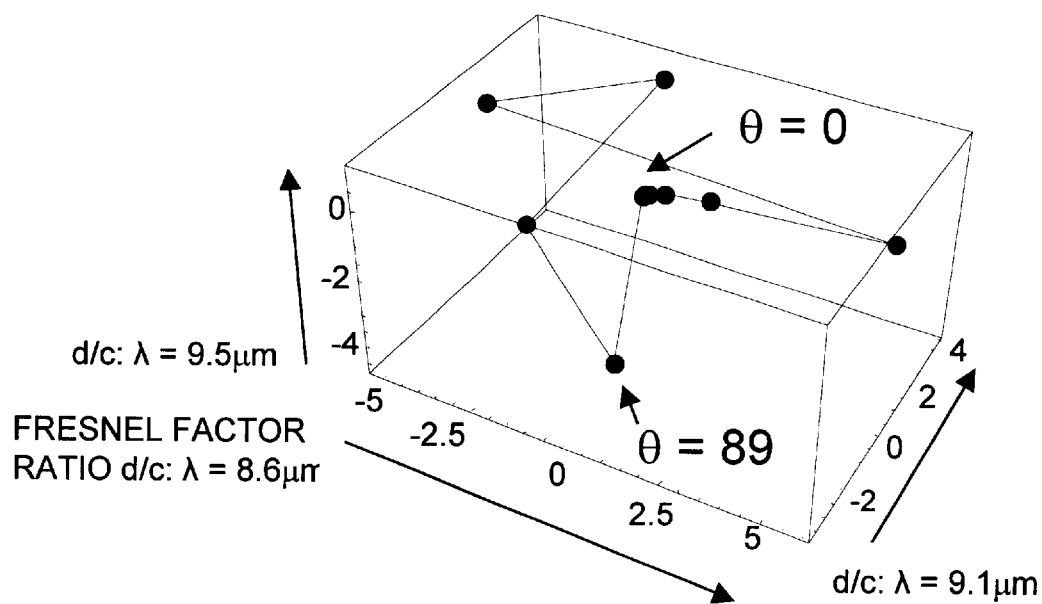
FIG. 10 depicts, for several incidence angles, resultant vectors of which each component is the ratio of the Fresnel reflectance factor d to the Fresnel reflectance factor c at a different one of three wavelengths.

FIG. 4 illustrates such a selection. It plots, for various spectral positions across a Lorentzian resonance, both the complex index of refraction and, for various angles of incidence $\theta$, the ratio of the Fresnel reflectance factors $d_{\theta,\lambda}$ to $c_{\theta,\lambda}$ that the refractive index dictates in accordance with Equation (4). (The plot clamps any ratio value to zero for which either $d_{\theta,\lambda}$ or $c_{\theta,\lambda}$ is less than 0.01). The particular resonance feature shown in the drawing loosely mimics the quartz reststrahlung feature near 9 micrometers wavelength. This plot indicates that the two necessary conditions identified above are indeed satisfied if the sample set's spectral locations are chosen judiciously. Against this particular resonance feature, the illustrated embodiment uses the four depicted spectral locations ($\lambda$ values) 48 whose $d_{\theta,\lambda}$-to-$c_{\theta,\lambda}$ ratios best discriminate among different $\theta$ values. FIG. 10, which is a plot of $d_{\theta,\lambda 1}c_{\theta,\lambda 1}$ versus $d_{\theta,\lambda 3}/c_{\theta,\lambda 3}$, versus $d_{\theta,\lambda 4}/c_{\theta,\lambda 4}$ for each of ten $\theta$ values, shows the discriminability that the best three afford. These plotted points form a curve that can be parameterized by $\theta$. The curve generally runs counter-clockwise (with one loop) as the value of $\theta$ steps in 10-degree increments. The separation and therefore the discriminability among the various $\theta$'s is diminished for $\theta$ between 0° and about 20°.

In this example, in which the resonance is reasonably well isolated, the SNR is 200:1, and the resolution in $\theta$ and $\phi$ needs to be about 2°, four well-chosen spectral samples of the Stokes radiance are adequate in the Case 1 inference regime. In general, though, the optimal choice and number of samples will depend on the particular resonance feature as well as on application-dependent trade-offs between economy and performance (inference error). Increasing the number of spectral samples ("features") used for inference will tend to improve the noise-equivalent-differential-angle errors NEd $\phi$ and NEd$\theta$ because they improve separability and, by averaging, reduce the effects of noise.

Beyond a certain number of features, though, performance will plateau or even decrease, as is well known to practitioners of pattern classification. This typically results from modeling infidelity or creep-in nuisance variability. For example, the surface-reflectance specular lobe of unknown finite width will induce averaging of the Fresnel reflectance factors over a range of $\theta$ and thereby "blur" the $\theta$ signature. This imposes a practical limit on NEd$\theta$ and NEd$\phi$ independently of the sensor noise level or the number of features employed.

Joint Inference of ($\theta,\phi$): Performance and Regime of Applicability

Situations that lie outside the "Case 1" regime of applicability share one or more of the following conditions:

The measured Stokes radiance component V'$_r$ is near zero (whenever either $d_{\theta,\lambda}$ or $U_{i,\lambda}$ is near zero as indicated by Equation (14))

The Fresnel-reflectance-factor ratio $d_{\theta,\lambda}$ to $c_{\theta,\lambda}$ does not vary enough for given $\theta$ within the employed set of spectral samples The spectral variation of Fresnel-reflectance-factor ratio $d_{\theta,\lambda}$ to $c_{\theta,\lambda}$ does not vary enough for different $\theta$ values.

The conditions "near zero" and "insufficiently" are defined by the specific application domain, but are strongly driven by the measurement SNR. For a sensor noise-equivalent DoP=0.5% (nominally 200:1 SNR), NEd$\phi$ or NEd$\theta$ markedly increases (e.g., beyond 5°) when the surface-incident polarization is too "weak" to produce enough elliptically polarized reflected radiance V'$_r$. Weak here means that the DoP of the surface-incident radiation is low and its AoP value is near 0° or 90°. The closer AoP is to 0° or 90°, the higher-valued DoP must be to exceed the "weak" threshold. For example, surface-incident radiation whose DoP is lower than 5% would always be considered weak in this context, and a DoP less than 10% results in weak polarization when AoP=15°. NEd$\phi$ or NEd$\theta$ also increases markedly for values of $\theta$<20°. This effect worsens for "weaker" surface-incident polarization states.

Fortunately, even though the surface-incident polarization state is unknown, misleading inferences are avoidable, because these situations are signaled by near-zero values of V'$_r$, larger variances for $\phi$, and/or shallower or broader minimums in plots of standard deviation of $\phi$ versus $\theta$. The regime of the Case 1 inference technique's validity is therefore application-dependent and can be predetermined by simulation.

Case 2: Inferring $\phi$ for Non-Obliquely Polarized Illumination ($U_{i,\lambda}$=0)

In most applications, values of V$_r$' and the variations in $\phi$ that result from using the Case 1 approach will indicate that the measurement conditions are indeed those of Case 1 and that its results can be relied on. If they do not, though, the illustrated embodiment turns to a second approach. This approach is based on the assumption that is $U_{i,\lambda}$=0, i.e., that the surface-incident illumination is weakly polarized or that its AoP is near 0° or 90°. This approach infers $\phi$ separately from $\theta$. We consider $\phi$ first.

The assumption that $U_{i,\lambda}$=0 simplifies Equation (14) to Equation (16):

$$\begin{bmatrix} - \\ Q'_r \\ U'_r \\ V'_r \end{bmatrix}_\lambda = \begin{bmatrix} - & - & - & - \\ 0 & \text{Cos}2(\gamma-\phi) & \text{Sin}2(\gamma-\phi) & 0 \\ 0 & -\text{Sin}2(\gamma-\phi) & \text{Cos}2(\gamma-\phi) & 0 \\ 0 & 0 & 0 & 1 \end{bmatrix} \quad (16)$$

$$\begin{bmatrix} - \\ \tau_\lambda k_{\theta,\lambda}\{(b_{\theta,\lambda}I_{i,\lambda}+a_{\theta,\lambda}Q_{i,\lambda})-b_{\theta,\lambda}L_\lambda\} \\ 0 \\ 0 \end{bmatrix}$$

Solving Equation (16) for angle $\phi$ yields Equation (17). As was true of the corresponding Case 1 expression, this expression is remarkably independent of nuisance variability.

$$\phi = \gamma \pm \frac{1}{2}\text{ArcCos}\left[\frac{\pm Q'_r}{\sqrt{Q'^2_r+U'^2_r}}\right] \quad (17)$$

$$\phi = \gamma + \frac{1}{2}\text{ArcTan}\left[\frac{U'_r}{Q'_r}\right]+\begin{Bmatrix} 0 \\ 90 \end{Bmatrix}$$

From inspection, Equation (15) simplifies to Equation (17) when the surface-emanating Stokes component V'$_r$ is zero, as it is when the Case 2 assumption, $U_{i,\lambda}$=0, prevails. Equation (17) can be expressed (as shown) in a manner that eliminates one of the two sign ambiguities. To apprehend this, Equation (16) shows that, in the surface-plane-of-incidence reference frame (i.e. prior to applying the rotation matrix), the emanating Stokes components U$_r$ and V$_r$ are zero. This indicates that the emanating AoP (determined by Q$_r$ and U$_r$) is constrained to be either zero or 90°, depending on the polarity of Q$_r$ (cf: Equation (5)). But the sign of Q$_r$ is, upon applying the rotation matrix (Equation (16)), imparted to both the numerator (U'$_r$) and denominator (Q'$_r$) in the Arc-Tan[ ]-based solution for $\phi$ in Equation (17). So that is canceled out and is thus lost to observation. This solution must therefore be augmented with the 90-degree-ambiguity term.

Figure 11:
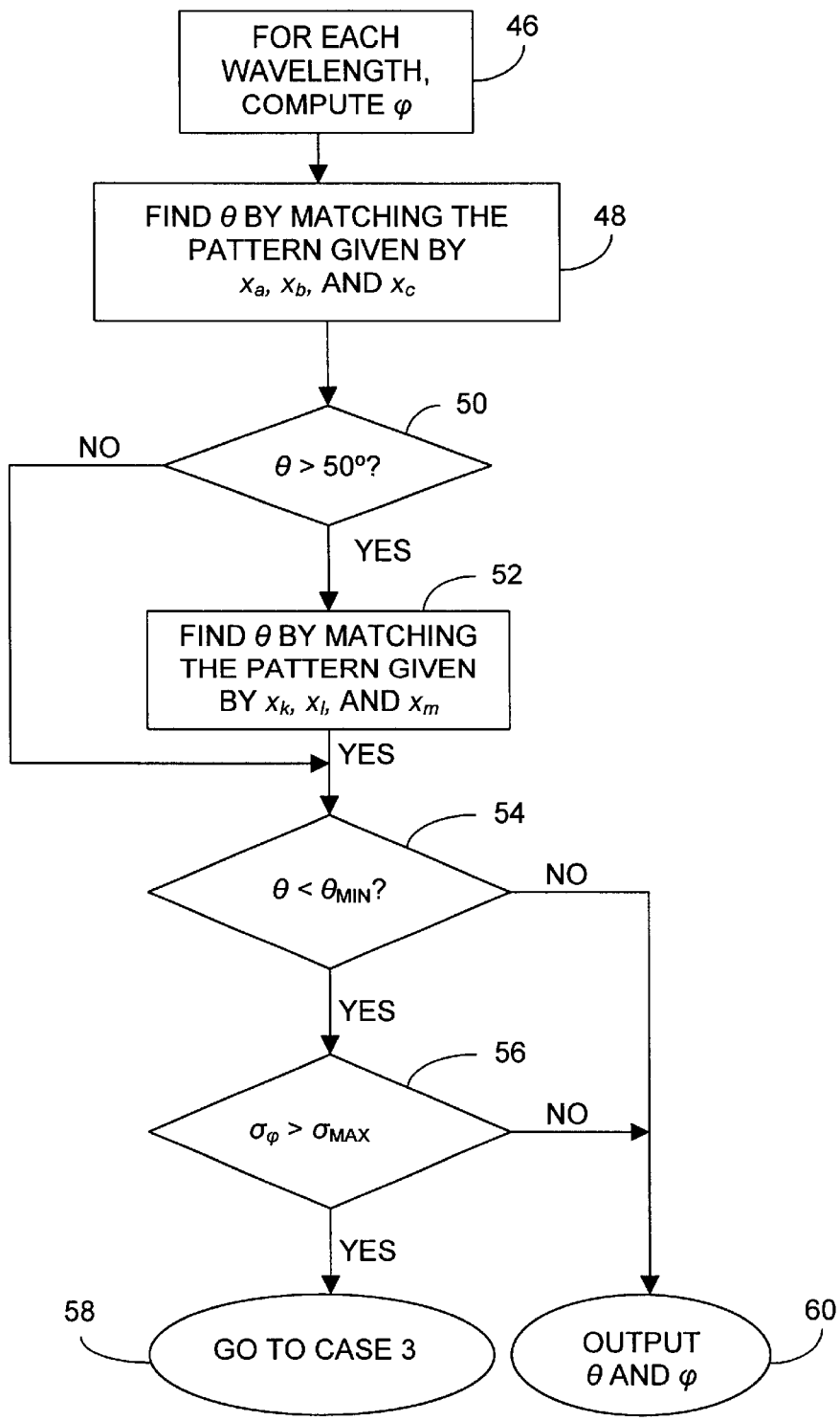
FIG. 11 is a flow chart depicting another technique that the illustrated embodiment employs to infer a surface's orientation from spectro-polarimetric measurements of the light received from that surface.

For Case 2, therefore, the apparent AoP ("appAoP," computed from Q'$_r$ and U'$_r$) measured in the sensor frame conveys $\phi$ with a 90-degree ambiguity. Application-specific information can often dispel this ambiguity. In the case of non-glowing objects measured in the visible band, for instance, if the degree of the illumination's polarization is low ($b_{\theta,\lambda}I_{i,\lambda}$ dominates $a_{\theta,\lambda}Q_{i,\lambda}$ in Equation (16)), then the polarity of $Q_r$ is positive since thermal emission $L_\lambda$ is zero. FIG. 11, which is a flow chart of the technique employed for Case 2, employs block 46 to represent computing $\phi$ in this manner from the radiance quantities at each of a number of wavelengths.

Simulations show the Case 2 regime to be desirably complementary to Case 1. Whereas Case 1 is inapplicable for surface-incident AoP near 0° or 90°, this is where Case 2's $\phi$-inference error is minimum. At least for the surface-incident condition DoP=30% and AoP=5°, the error is largely independent of (true) $\phi$ and somewhat dependent on $\theta$.

Case 2: Inferring $\theta$ for Non-Obliquely Polarized Illumination ($U_{i,\lambda}=0$)

We now turn to the Case 2 determination of the angle of incidence $\theta$. Unlike its determination of the rotation angle, Case 2's angle-of-incidence determination depends upon the Fresnel reflectance factors'spectral behavior across a resonance. As will be explained presently, the dependence in this case is on the spectral behavior of the Fresnel reflectance factor $b_{\theta,\lambda}$ (rather than factors $d_{\theta,\lambda}$ and $c_{\theta,\lambda}$ as in Case 1). As was mentioned above, FIG. 5 depicts the spectral behavior of the Fresnel reflectance factor $b_{\theta,\lambda}$ across a sufficiently isolated Lorentzian resonance for various angles of incidence. It shows a generic bimodal ("double-bump"') feature. In the Case 2 regime, the illustrated embodiment exploits the fact that the relative heights of these bumps change characteristically with the angle of incidence $\theta$. The shorter-wavelength bump is higher than the longer-wavelength bump for near-normal incidence ($\theta$ near 0°), whereas the longer-wavelength bump becomes higher than the shorter-wavelength one toward grazing incidence ($\theta$ near 90°). The illustrated embodiment exploits the fact that this behavior can be seen in measured Stokes components $Q_r'$ and $U_r'$.

Equation (16) shows that the expression for the measured Stokes components $Q'_r$ and $U'_r$ are both linear combinations of Fresnel reflectance factors $b_{\theta,\lambda}$ and $a_{\theta,\lambda}$. Factor $b_{\theta,\lambda}$ spectrally modulates the difference between the surface-incident-illumination and thermally self-emitted intensities, while $a_{\theta,\lambda}$ spectrally modulates the polarized surface-incident illumination intensity $Q_{i,\lambda}$. Moreover, the $Q'_r$ and $U'_r$ radiance spectra are replicas of each other, scaled in a fixed proportion determined by $\gamma-\phi$, the aggregate coaxial rotation angle between the surface and sensor reference frames. The degree of polarization (DoP) of the surface-incident illumination determines the balance between the influences of $b_{\theta,\lambda}$ and $a_{\theta,\lambda}$ on $Q'_r$ and $U'_r$: $a_{\theta,\lambda}$'s contribution is negligible at DoP=0%, while $b_{\theta,\lambda}$'s contribution is negligible at DoP=100%. For lower values of DoP, therefore, measured quantities $Q_r'$ and $U_r'$ both exhibit the bimodal behavior in which the relative heights indicate what $\theta$'s value is. The Case 2 approach therefore bases its inference of $\theta$ on those quantities and is therefore applicable only for the lower-DoP regime.

Since these bumps'relative heights is what conveys the angle of incidence $\theta$, the inference of $\theta$ from the Stokes radiance spectrum is invariant to the unknown scale and level of the emanating polarized radiance. This is valid at least for low values of surface-incident DoP, where $b_{\theta,\lambda}$ dominates $a_{\theta,\lambda}$. Due to this "self-normalizability," the inference of $\theta$ is robust against most of the previously mentioned sources of nuisance variability, such as surface roughness, path transmittance, and illumination intensity (including emission/reflection-balance ambiguity). Since the shapes of $Q_r'$ and $U_r'$ as functions of wavelength are the same but have relative magnitudes that depend on $\gamma-\phi$, the illustrated embodiment combines them in a function $x(\lambda)=|Q_r'(\lambda)|+|U_r'(\lambda)|$ and uses that function's shape as an indicator of $\theta$'s value, although other functions could be used instead. Specifically, the illustrated embodiment employs a subset of spectral samples $x_j$ as a measurement (or "feature") vector X. The value of $\theta$ is inferred by evaluating a decision function F[X] that maps X to $\theta$'s value.

The set of spectral samples available to compose X defines a so-called feature space (or pattern space). For effective inference, the decision function F[X] should be rendered invariant to unknown nuisance variables, the most common of these being the variable scale and offset of the measurement samples $x_j$. The sources of nuisance variability in scale have been discussed earlier. An unknown (spectral-average) offset due to unmodeled effects may also be present.

To achieve the desired invariance to scale and offset, I self-normalize the measurement vector X in accordance with Equation (18) (where j is the sample index):

$$\tilde{x}_j = \frac{x_j - \min[X]}{\max[X] - \min[X]} \quad (18)$$

Figure 12:
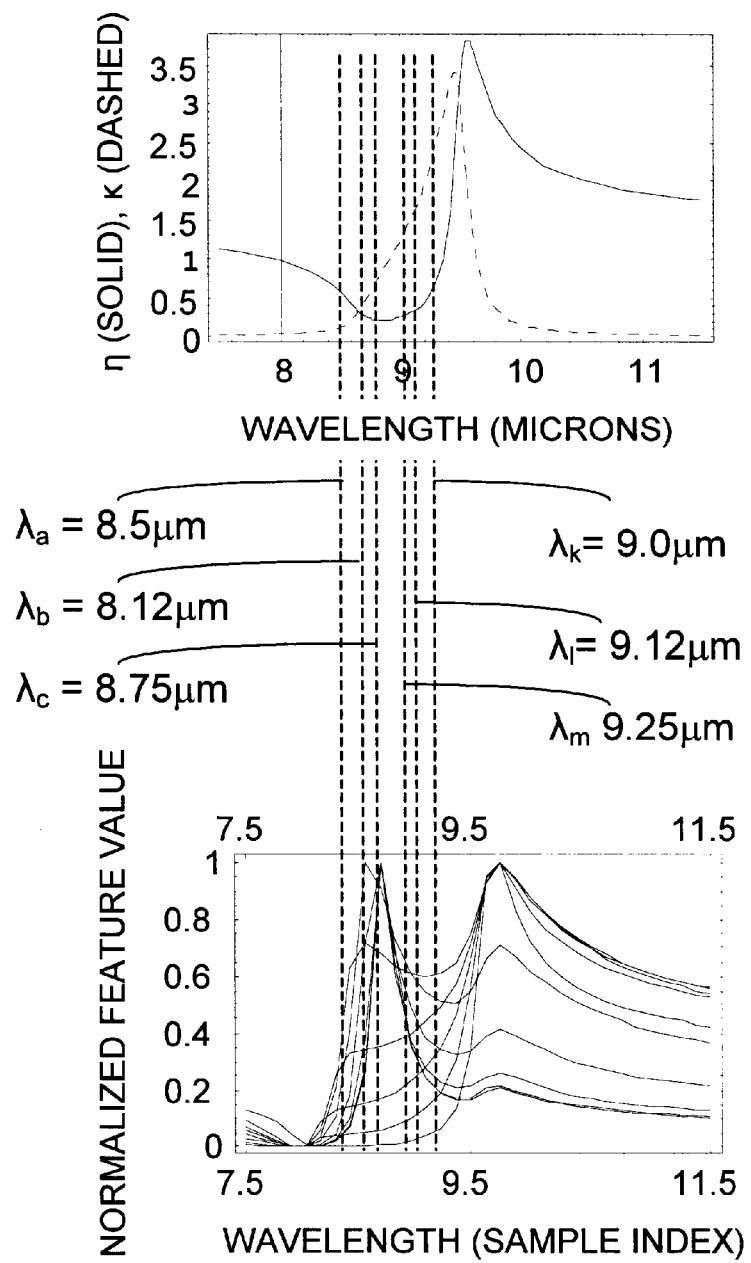
FIG. 12 is a diagram that plots, for several incidence angles, the value, as a function of wavelength, of one component of a feature vector employed for pattern matching by one of the illustrated embodiment's orientation-inference techniques.

FIG. 12 plots, for various spectral positions across a Lorentzian resonance, both the complex index of refraction and, for various angles of incidence $\theta$, the normalized feature samples that Equation (18) defines. The latter plots are composed of thirty-two uniformly-spaced spectral samples across a Lorentzian resonance. For simplicity, all thirty-two samples were employed for self-normalization, although it would have sufficed to use only a handful of fixed samples chosen to maximize the expected denominator in Equation (18) and thus reduce normalization sensitivity to measurement noise.

In addition to scale and offset, the decision function F[X] must also be rendered (to the extent possible) invariant to the unknown DoP of surface-incident illumination. DoP causes a deterministic "distortion" of the feature vectors. This distortion is due to unknown mixing between Fresnel reflectance factors $b_{\theta,\lambda}$ and $a_{\theta,\lambda}$. Since $a_{\theta,\lambda}$ is not even nearly orthogonal to $b_{\theta,\lambda}$ (for any fixed $\theta$ when thirty-two samples across a Lorentzian resonance are used), invariance cannot be achieved by orthogonal-projection methods. Instead, the illustrated embodiment employs a quadratic-distance classifier tuned to maximize the achievable invariance, as will be described below.

Figure 13:
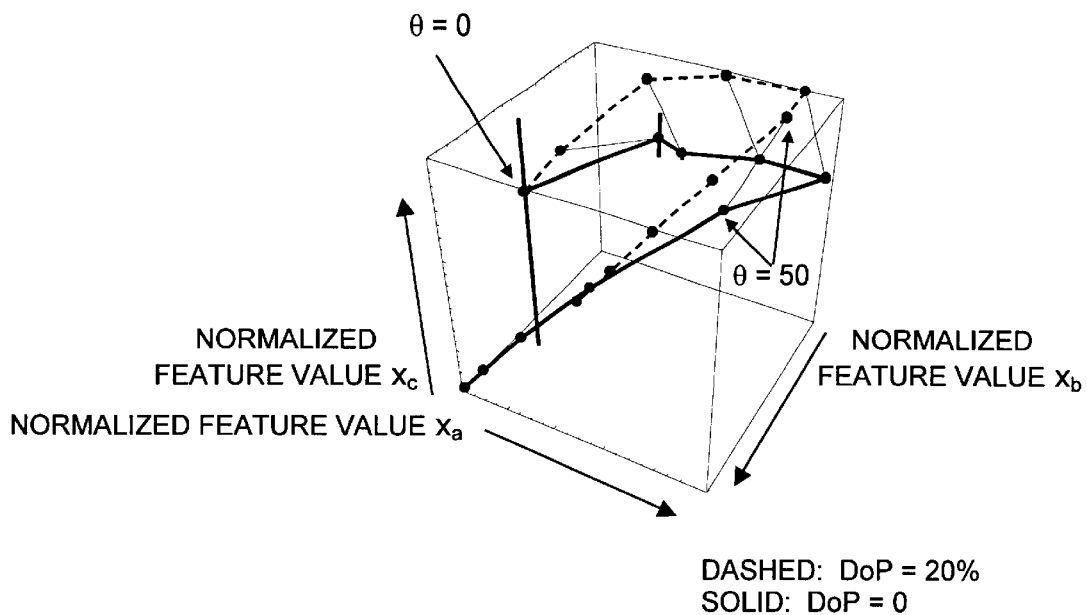
FIG. 13 depicts that feature vectors as a function of incidence angle for two different degrees of polarization.

FIG. 12 shows, for the particular resonance feature that it plots, the wave-lengths $\lambda_a$, $\lambda_b$, and $\lambda_c$ of the three samples $\{x_a, x_b, x_c\}$ best positioned to distinguish among the $\theta$ values in the range of 0° to 50°. FIG. 13, which plots $x_a$ versus $x_b$ versus $x_c$ for each of the ten $\theta$ values, demonstrates the resultant discriminability of $\theta$. It includes two such curves, each of which can be parameterized by $\theta$. The solid-line curve corresponds to a surface-incident DoP of 0%, while the dashed-line curve corresponds to a DoP of 20%. The curves run clockwise from center-left to lower-left as the value of $\theta$ steps in 10° increments.

Two factors determine the discriminability of $\theta$: (a) the separation between the points along the same, solid-line curve or dashed-line, curve, and (b) the nature of the "offset" of the dashed-line curve from the solid-line curve, characterizing the "distortion" of the feature vectors as DoP increases from 0 to 20%. Regarding the first factor, the inter-point separation is gauged relative to random deviation due to sensor noise. The half-length of the thick black vertical line drawn through each point on the solid line (but not visible for most points, since they are obscured by the thickness of the plotted points themselves) indicates the noise deviation for a sensor SNR of 200:1 (reckoned in the unnormalized measurement space). Because the scale of the denominator in Equation (18) varies with θ, the equivalent noise deviation in the normalized feature space $\{x_a, x_b, x_c\}$ similarly varies.

Figure 14:
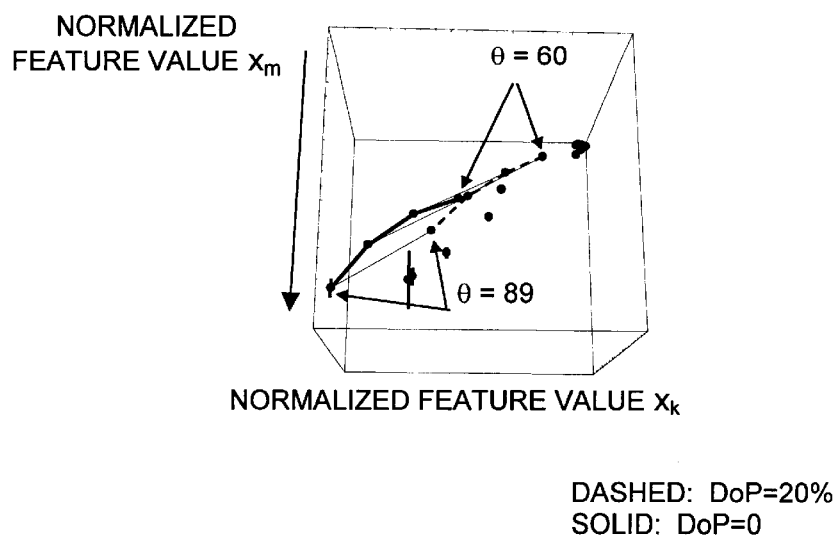
FIG. 14 is a similar diagram of a different feature vector.

From the relative separation of points as gauged by noise in FIG. 14, one can estimate a "noise-equivalent differential θ," or "NEdθ." An extreme normalized noise deviation is depicted for θ=0°, which is due to zero polarizance (and thus zero polarized radiance) at θ=0. Nevertheless, this condition (θ near zero) can be detected in preprocessing by looking for a spectrally flat, noise-magnitude polarized radiance. For θ between 0° and 10°, NEdθ is approximately 5°, decreasing to about NEdθ=1° (i.e., the width of the plotted points) beyond θ=20°. The actual NEdθ will also vary with the unknown signal level, which for instance may be reduced by surface roughness. Thermal infrared sensing of the surface in temperature equilibrium with its surrounding illumination (i.e., comparable values of $I_i$ and L in Equation (16)) would measure negligible polarized radiance.

The second factor determining the discriminability of θ is the nature of the "off-set" of the dashed-line curve from the solid-line curve. That factor characterizes the "distortion" of the feature vectors as unknown surface-incident DoP increases from 0 to 20%. The feature vector $X_θ$[DoP], corresponding to a given value of θ and DoP, traces a curve in feature space as DoP is varied. The tangent vector to this curve, approximated by the line segment between $X_θ$[20%] and $X_θ$[0%], is characteristic of the distortion due to DoP. Such tangent vectors are depicted in FIG. 13 as thin lines connecting the corresponding points of the solid- and dashed-line curves. The decision function F[X] should therefore estimate θ, for a point X lying between the solid and dashed-line curves, by finding or interpolating between the nearest tangent vectors. Such use of the tangent vectors makes the inference of θ invariant to unknown DoP (cf: "Tangent Distance Classifier" pp.188–192 DudaHart2001).

However, to maintain insensitivity to the unknown distortion, the tangent vectors should ideally be (a) parallel to one another, and (b) orthogonal to the dashed-line and solid-line curves (cf: FIG. 13). This is essentially the case for the tangent vectors corresponding to θ values spanning 0°–50°. So, as FIG. 11's block 48 indicates, the processor derives a θ value by matching against feature vectors that result from measurement at $λ_a$, $λ_b$, and $λ_c$.

In FIG. 13, tangent vectors for θ values spanning 60°–89° are purposely not shown, because these segments of the solid- and dashed-line curves are highly "skew off-set." This skewness draws the corresponding tangent vectors close to one another, rendering any inference in this region highly susceptible to noise. So, if the illustrated embodiment finds that the feature vector is in this region of that vector space, it rejects the inference as unreliable, as block 50 indicates.

Fortunately, there exists a different set of three wavelengths $λ_k$, $λ_l$, and $λ_m$ at which the three samples $x_k$, $x_l$, and $x_m$ can be taken that are best positioned to distinguish among the θ values in the range of 60° to 89°. As FIG. 11's blocks 50 and 52 indicate, therefore, the illustrated embodiment uses such samples if it has determined the original θ inference was unreliable. FIG. 14, which plots $x_k$ versus $x_l$ versus $x_m$ for each of the ten θ values, demonstrates θ's discriminability in the 60–89 degree region. The dashed-line and solid-line curves connect only the points corresponding to θ between 60°–89°. Both the separability of these points and the nature of their tangent vectors are quite favorable, yielding a NEdθ=1°. Moreover, the θ<60 and θ>60 regimes do not overlap within either feature subspace $\{x_a, x_b, x_c\}$ or $\{x_k, x_l, x_m\}$. This indicates a favorable, unambiguous decision-regime "cross-over."

For this exposition, merely six well-chosen spectral samples of the Stokes radiance are enough for to infer θ, although additional samples may be used for self-normalization. The optimal choice and number of samples will depend on the particular resonance feature as well as on application-dependent trade-offs between economy and performance (e.g., NEdθ). Again, increasing the number of spectral samples ("features") used for inference will tend to improve NEdθ up to a point. After that, performance will plateau or even decrease, as was explained above.

The choice of the optimal set and number of features is the "feature selection" problem. Although many feature-selection methods are available, it is best for the chosen method to employ a quadratic distance measure that admits distinct class-conditional covariance matrices, to handle multiple classes, and to maximize interclass margins as a principal criterion [IannarilliRubin2002]. Such a method was employed to select the three best features discussed earlier. The method was purposely "tuned" to select features that yield both large inter-class (θ) separations and well-conditioned (parallel, non-skew) tangent vectors. This was done by constructing each class-conditional covariance matrix with tangent vector $X_θ[20\%]-X_θ[0\%]$ as one of its eigenvectors and by defining $X_θ[10\%]$ as the class-conditional mean vector. Without using the tangent vectors or tuning them in that way, the unknown distortion due to variable surface-incident DoP would increase the θ inference error to well beyond 10° across much of its range.

Case 2 θ Inference: Regime of Applicability

Figure 15:
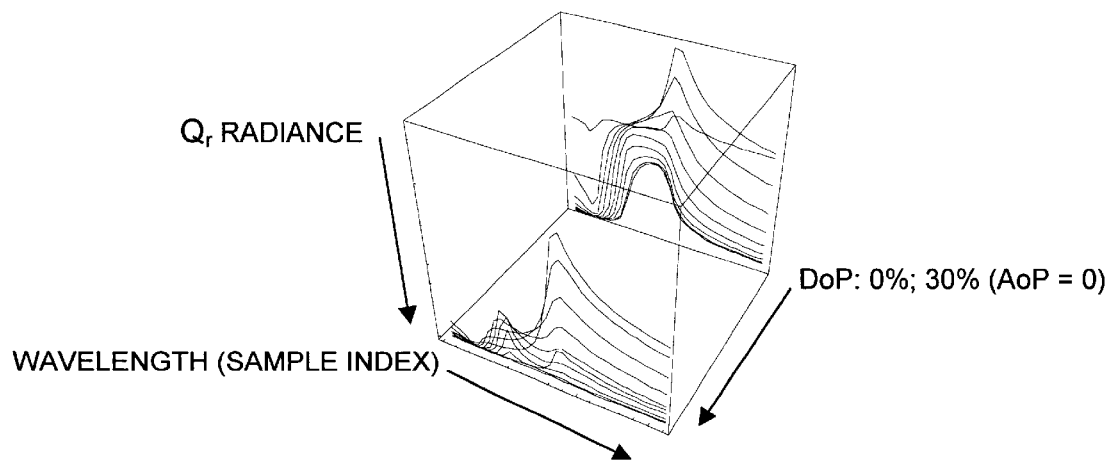
FIG. 15 is a diagram depicting the behavior of one Stokes radiance component as a function of wavelength for various incidence angles at two different degrees of polarization.

We now ascertain the sensitivity of the θ inference to the surface-incident illumination's (unknown) DoP and AoP. FIG. 15 plots the way in which the Stokes spectral radiance $Q'_r$ (and $U'_r$) changes with surface-incident DoP. The front family of curves is plotted against wavelength for various angles of incidence for DoP=0%, while the rear family is similarly plotted for DoP=30%. In both cases, AoP=0°. $Q'_r$ transitions from bimodality to unimodality with increasing DoP (mirroring the behavior of "perpendicular" Fresnel term $ρ_s*ρ_s$). Much of the bimodality is disrupted when DoP reaches 30%. In some embodiments of the invention, enough (fine-resolution) spectral samples may be taken to distinguish θ from a decidedly unimodal $Q'_r$ on the basis of the micro-details in its shape patterns. But this is not nearly as desirable as operating in the low-DoP, bimodal regime, which requires substantially less SNR and fewer spectral samples for well-conditioned inference processing.

Figure 16:
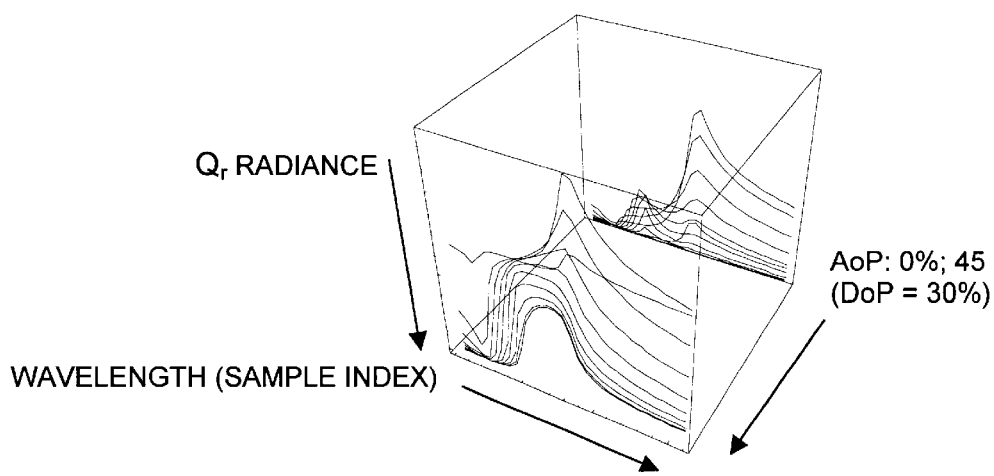
FIG. 16 is a diagram depicting the behavior of one Stokes radiance component as a function of wavelength for various incidence angles at two different angles of polarization.

Although the Case 2 inference regime is formally defined when $U_{i,λ}$=0 (surface-incident illumination AoP=0° or 90°), its practical boundaries are determined by the tolerable deviation of AoP about 0° or 90°. The measured $Q'_r$ and $U'_r$ radiance spectra are linear combinations of $Q_r$ and $U_r$, with weightings determined by γ–φ (cf: Equation (9)). Recall that the unprimed symbols $Q_r$ and $U_r$ are surface-emanating Stokes radiance components referenced to the surface plane of incidence, i.e., prior to applying the rotation matrix. FIG. 16 plots how $Q_r$ changes with surface-incident AoP. The front family of curves is plotted versus wavelength for various angles of incidence for AoP=0, while the rear family is similarly plotted for AoP=45°. In both cases, the DoP is 30%. For AoP not 0° or 90°, Equation (9) applies (rather than Equation (16)), with resultant surface-emanating Stokes spectral radiance $U_r$ mirroring the spectral pattern of Fresnel reflectance factor $c_{\theta,\lambda}$. The $Q_r$ term, for DoP less than about 20%, manifests the self-normalizable bimodal behavior that conveys $\theta$. The $U_r$ term acts as an unknown additive interference. The magnitude of the $U_r$ term increases with DoP and as AoP approaches 45° or 135°. At DoP=20% and AoP=15°, $U_r$ is no more than ~2% of $Q_r$ which for a sensor SNR of 200:1, this implies that the absolute-value sum of $Q'_r$ and $U'_r$ differs minimally from $Q_r$ with respect to noise. If surface-incident DoP is sufficiently small, therefore, Case 2 inference of $\theta$ can be effective even at AoP values near 45° or 135°, which is well outside the formally defined Case 2 regime.

As FIG. 11's block 54 indicates, therefore, the processor determines whether the inferred $\theta$ value is less than a minimum, which is 30° in the illustrated embodiment. If it is, the measurements may have been then in a regime where they tend to be unreliable. To check this, the processor determines whether the $\phi$ values derived in step 46 varied too much to be considered reliable, as block 56 indicates. If so, the processor proceeds to the inference technique associated with Case 3, as block 58 indicates. Otherwise, as block 60 indicates, the $\phi$ and $\theta$ values inferred in the FIG. 11 technique are output as the surface's orientation.

Case 3: Inferring $\phi$ for Weak Obliquely Polarized Illumination and Small $\theta$ For sensor SNR of 200:1, the Case 1 and Case 2 methods both fail to retrieve $\phi$ when the following two conditions prevail simultaneously: (a) the unknown surface-incident illumination's DoP is small (e.g., 0–10%) and obliquely polarized (e.g., AoP removed from 0° or 90°), and (b) $\theta$ is small, generally less than 30°. In this regime, which we define as "Case 3," $\theta$ can be effectively retrieved by using the Case 2 method. The $\theta$ value thus obtained can then be used in Equation (15), together with the $\phi$ ambiguity and variance-minimizing techniques from Case 1, to retrieve $\phi$. I have found that, if the inferred $\theta$ value is less than 20°, employing a value of 20° in solving Equation (15) for $\phi$ yields better-stabilized solutions. Moreover, one should employ a relaxed SNR threshold of 1:5 (instead of Case 1's 4:1). For $\theta$ in the range of 5°, the NEd$\phi$ is 10° or greater, whereas it is about 5° for $\theta$ greater than 10°.

Utilizing Refractive Index Resonance Features

The methods of the subject invention for inferring $(\theta,\phi)$ proceed from presumed knowledge of the complex refractive index spectrum $n_\lambda$ across one or a plurality of its resonance features. This presumption in turn seems to imply the need for detailed a priori knowledge of the surface under observation. Such a requirement would rule out many practical applications. Even knowing the generic chemical identity of the surface, and thus its nominal refractive-index spectrum from a physical handbook, may not suffice. Variables such as surface preparation and oxidation may cause the spectrum to change significantly from nominal values.

Fortunately, the invention's foundational elements provide a way to infer the complex refractive-index spectrum $n_\lambda$ from spectral measurements of the polarization state. With $n_\lambda$ thus known, $(\theta,\phi)$ can be inferred from the same or similar measurements in the manner described above.

Prerequisite Characteristics of a Utilizable Resonance Feature

Before we discuss how to infer $n_\lambda$ from spectral polarization-state measurements, we will discuss the kinds of resonances that can be used for $(\theta,\phi)$ inference. Not all resonance features are suitable for practicing the subject invention. Some, though observable in measurements, may simply not exhibit the "strength" necessary to manifest the characteristic features in the Fresnel reflectance factors at sufficient signal-to-noise ratio.

As discussed earlier, a prerequisite characteristic of a resonance suitable for the Case 1 methodology is that the spectral variation of the ratio of Fresnel reflectance factors $d_{\theta,\lambda}$ to $c_{\theta,\lambda}$ must differ among various $\theta$ values, as FIG. 4 illustrates. This ratio is computed for a given resonance by using Equation (4) with the complex refractive index spectrum $n_\lambda$.

The prerequisite characteristics of a resonance suitable for Case 2's $\theta$-inference methodology are generally more restrictive than for Case 1. The criterion is that $n_\lambda$ manifest the self-normalizing bimodal ("double-bump") feature in the spectrum of the Fresnel reflectance factor $b_{\theta,\lambda}$. Not all resonance features satisfy that criterion.

Figure 17:
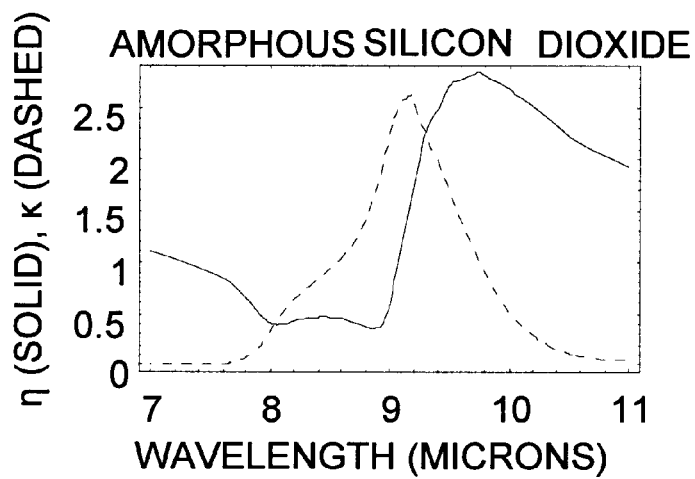
FIG. 17 is a diagram that plots both complex index of amorphous silicon dioxide's index of refraction as a function of wavelength and also, for various incidence angles, the resultant value of the Fresnel reflectance factor b.
Figure 17:
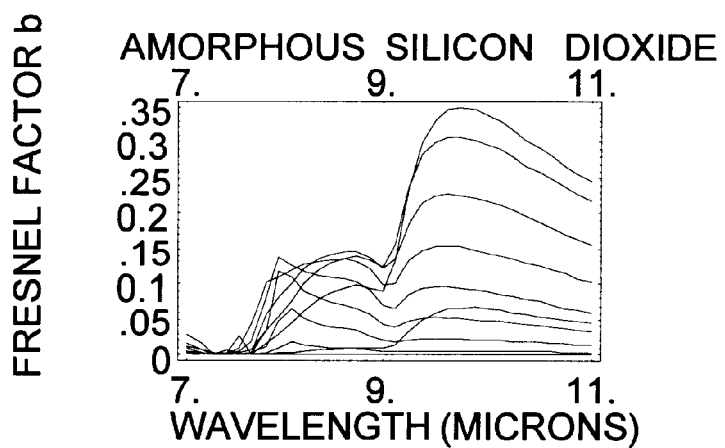

The most unambiguous and useful bimodal feature is manifested by a well-isolated Lorentzian resonance [Wooten1972, Ward1994], whose complex refractive index behaves in a manner similar to that depicted in FIG. 7. But the resonance's behavior need not match the FIG. 7 behavior exactly. As FIG. 17 shows for amorphous silicon dioxide's refractive-index resonance near 9 microns, somewhat-different refractive-index behavior yields a Fresnel reflectance factor $b_{\theta,\lambda}$ whose desirably bimodal spectrum changes characteristically with the angle of incidence $\theta$.

Figure 18:
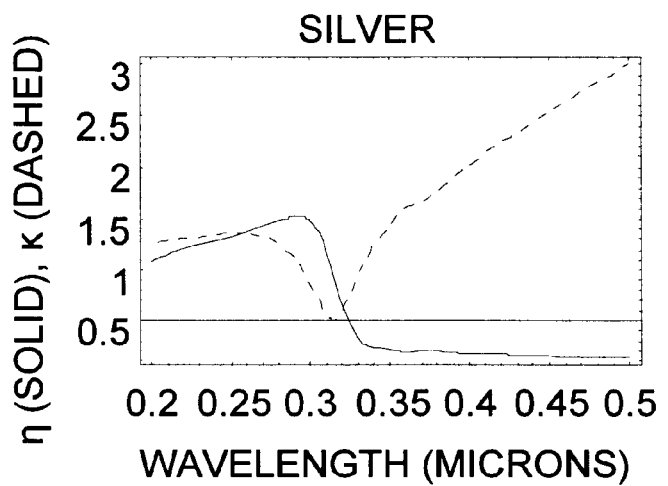
FIG. 18 is a similar diagram for silver.
Figure 18:
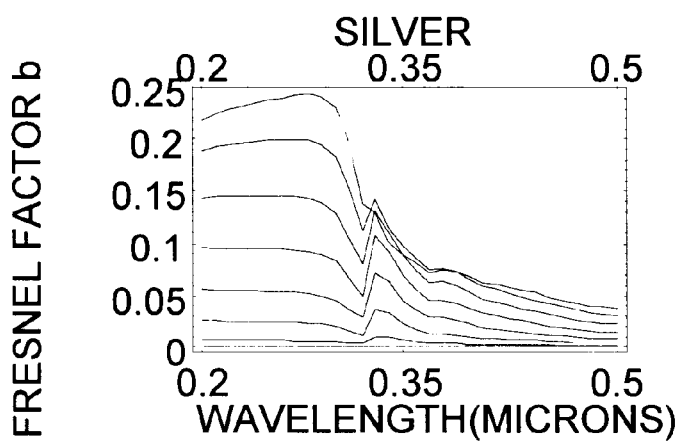

The pursuit of distinct spectro-polarimetric modulation patterns that change characteristically with angle-of-incidence $\theta$ can extend beyond Lorentzian resonances. For a metal or semiconductor, for instance, the refractive index's real part $\eta$ crosses the imaginary index $\kappa$ (in accordance with the Drude model [Wooten1972, Ward1994]) at the material's plasma frequency. FIG. 18 demonstrates this, plotting silver's complex refractive index near 0.3 microns and, for several incidence angles, the resultant spectrum of the Fresnel reflectance factor $b_{\theta,\lambda}$. (But such a pattern's self-normalizability is arguably less robust than the self-normalizability of patterns that Lorentzian resonances exhibit.)

Figure 19:
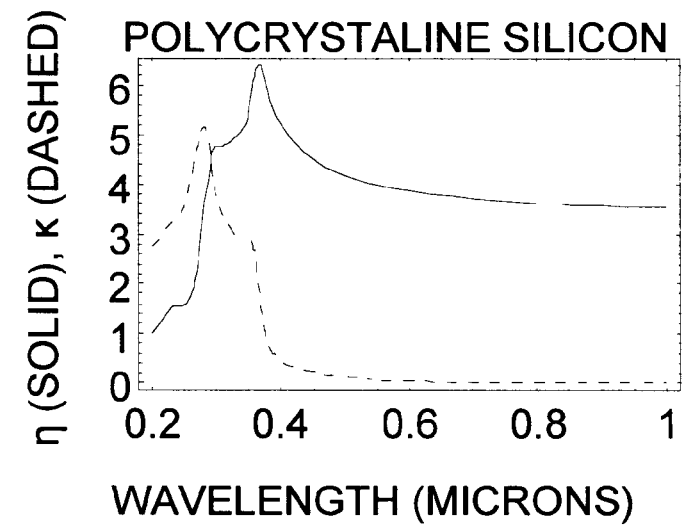
FIG. 19 is a similar diagram for polycrystalline silicon.
Figure 19:
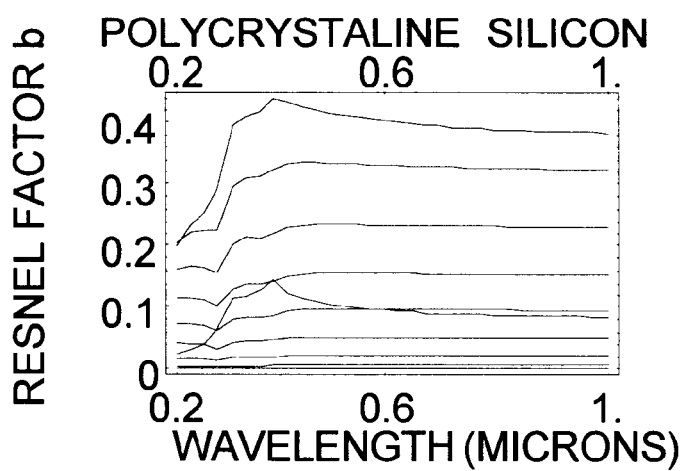

As FIG. 19 illustrates, on the other hand, polycrystaline silicon's resonance near 0.3 microns is not well suited to use in the Case 2 inference technique. The spectrum of its resultant Fresnel reflectance factor $b_{\theta,\lambda}$ exhibits little useful bimodality.

A clue to whether a given resonance is well suited for use in the Case 2 inference technique can be obtained from the relationship between the behaviors of the refractive index's real and imaginary parts. Note in FIG. 7 that the real part $\eta$ has decreased to unity or less before the imaginary part $\kappa$ begins to rise. This is favorable, for a reason that we now discuss.

First recall that the feature-vector components used in the Case 2 inference technique were so computed from measured quantities as to exhibit a spectral behavior similar to that of the Fresnel reflectance factor $b_{\theta,\lambda}$. Recall also that Equation (4) gives the value of that factor as a function of incidence angle $\theta$ and the (complex) index of refraction $(\eta,\kappa)$. For respective example incidence angles $\theta$=30° and $\theta$=70°, FIGS. 20 and 21 are surface plots of the Equation (4) relationship: they plot the Fresnel reflectance factor $b_\theta[\eta,\kappa]$ as a function of the refractive index's real and imaginary components $\eta$ and $\kappa$.

Figure 20:
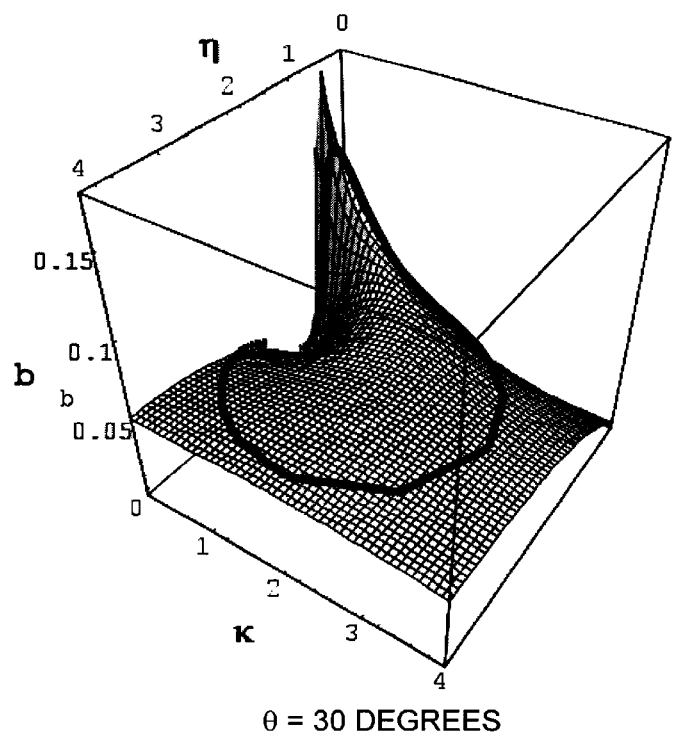
FIG. 20 is a surface plot of the Fresnel reflectance factor b as a function of the real and imaginary parts of a surface's complex index of refraction when the incidence angle is 30°.

For lower-valued $\theta$, exemplified by FIG. 20's $\theta$=30°, $b_\theta[\eta,\kappa]$ exhibits a peak near the origin (i.e., near where the values of $\eta$ and $\kappa$ are small). For higher-valued $\theta$, exemplified by FIG. 21's θ=70°, on the other hand, this peak in $b_\theta[\eta,\kappa]$ transforms into a trough. This large difference shows that factor's potential as an indicator of incidence angle.

Figure 21:
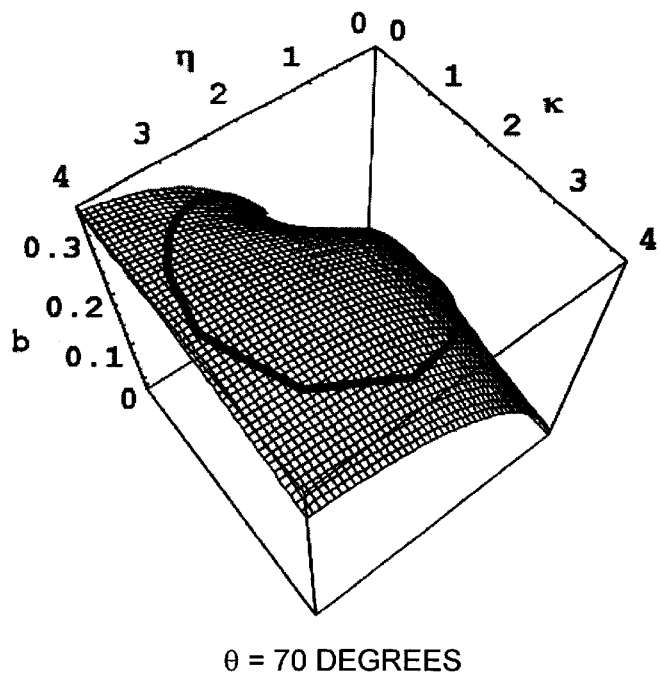
FIG. 21 is a similar surface plot for an incidence angle of 70°.
Figure 22:
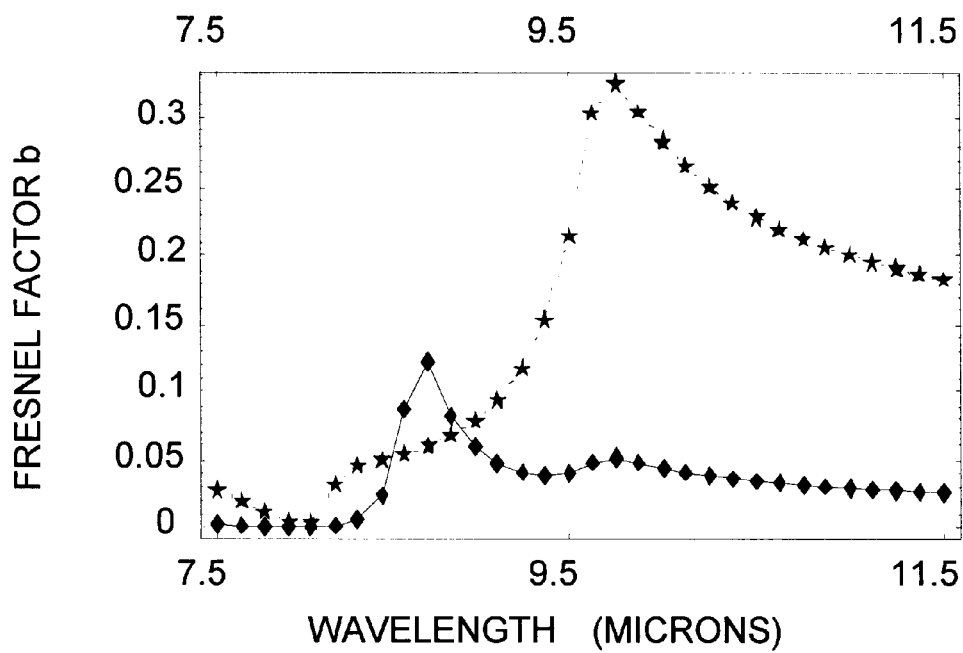
FIG. 22 is a diagram that plots Fresnel reflectance factor b as the functions of wavelength that result from the spectral trajectories depicted in FIGS. 20 and 21.

But it is important to note that the surface plots of FIGS. 20 and 21 merely depict the relationship given by Equation (4) between $b_\theta$ and $(\eta,\kappa)$ combinations, independently of whether those combinations actually occur in any material's refractive-index spectrum. That is, $\eta$ and rare the two independent plot variables, so most $(\eta,\kappa)$ combinations depicted by those drawings do not occur in any given material's refractive-index spectrum. Instead, the $(\eta,\kappa)$ combinations (and resultant values of $b_\theta$) exhibited by the example resonance of FIG. 7 are indicated by "spectral trajectory" curves superimposed on the surfaces that FIGS. 20 and 21 depict, while FIG. 22 plots the two resultant $b_\theta$ spectra. The spectral trajectory (parameterized by wavelength $\lambda$) winds clockwise with increasing wavelength, starting and ending with $\kappa=0$. Note that the trajectory in FIG. 20, i.e., the surface plot for $\theta=30°$, climbs high on the near-origin peak. Consequently, the low-θ-value-indicating peak is evident in the spectrum of $b_\theta$. As inspection of FIG. 20 reveals, this happens when the relationship between the $\eta$ and $\kappa$ spectra has the above-mentioned feature, i.e., when the real part $\eta$ has decreased to unity or less before the imaginary part $\kappa$ begins to rise. If that relationship does not prevail in the resonance's neighborhood, on the other hand, that resonance tends not to be well suited to use in the Case 2 incidence-angle-inference technique.

Inferring Refractive-Index Spectrum from Remote Measurements

We have so far assumed that the surface's refractive-index spectrum $n_\lambda$ is known a priori. In many potential applications, though, such knowledge is not available. In those applications, it is necessary to infer $n_\lambda$ from spectral-polarization-state measurements. Such an effort may appear ill-fated; lack of knowledge of the surface orientation and of nuisance-parameter values would seem to be obstacles. But I have recognized that this is not always—even usually—the case.

For one thing, some applications may admit of a "training" phase, in which known orientation values can be used to learn the $n_\lambda$ spectrum before that spectrum is used to determine unknown orientations. Even when a training phase is unavailable, though, I have found that "blind" estimation of $n_\lambda$, i.e., estimation without reliance on prior orientation knowledge, can be accomplished in a wide variety of situations. This is possible, as will presently be explained, because the underlying dimensionality of a refractive-index resonance is much lower than the explicit dimensionality of the spectral polarization measurements.

To appreciate this, consider the nature of the refractive-index spectrum. Despite potential complexity (thin-film interference effects in layered media [Ward1994], and sub-surface volume scattering [Hapke1993]), spectral resonance features are often quite generic in character. Equation (19) is a combined Drude-Lorentz-form model for the spectral "dispersion" of the complex index of refraction, which is the (complex) square root of the dielectric constant $\in$ in the optical region, where the magnetic permeability $\mu$ is typically 1 [Wooten1972, Ward1994]:

$$n\left[\frac{c}{\lambda}\right] = n[\nu] = \sqrt{\varepsilon[\nu]} = \sqrt{\varepsilon_\infty - \frac{\nu_p^2}{\nu^2 + i\nu_c\nu} + \sum_j \frac{c_j\nu_j^2}{\nu_j^2 - \nu^2 - i\Gamma_j\nu_j\nu}} \quad (19)$$

Here $\nu$ is optical frequency, c is the speed of light, and $i \equiv \sqrt{-1}$. The third term under the radical in Equation (19) is a sum of damped harmonic oscillators comprising the Lorentz-model form. Each summand is responsible for the ubiquitous resonance spectral behavior near its resonance frequency $\nu_j$. As was explained above, FIG. 7 shows a spectral plot of the real and imaginary components of the index of refraction across a well-isolated Lorentzian resonance, in which the ubiquitous resonance characteristic behavior is evident. The constant $\Gamma_j$ is the resonance peak's relative width expressed as a fraction of the resonance location frequency $\nu_j$. (Some forms of the Lorentz model combine constants $\Gamma_j$ and $\nu_j$ into a "damping" constant). The $c_j$ term in the numerator is a positive quantity known as the "strength" factor.

The second term under the radical in Equation (19) is the Drude-model form of dispersion due to free electrons. Note that the Drude form is a special case of the Lorentz form, with the resonance frequency set to zero. (Since the electrons are free, there is no restoring force.) The terms in the Drude model are the bulk plasma frequency $\nu_p$, which free-electron density determines, and a damping term, which is expressed as a mean collision frequency $\nu_c$. Finally, $\in_\infty$ is the high-frequency dielectric constant.

Despite the semi-classical origins of the Drude and Lorentz models, their functional forms also emerge from a full quantum-mechanical treatment of various material resonance mechanisms. A key point regarding Equation (19) is that estimation of no can be reduced to estimation of the appropriate resonance parameters. We discuss below how to estimate these parameters from polarimetric measurements.

Now, the resonance-parameter-estimation technique presently to be discussed depends on making measurements of radiation reflected from the target surface at a variety of reflection angles θ, so radiation received from a variety of directions $(\alpha,\beta)$ will be measured. Since this means that radiation will be received from different parts of the object, it may be received from surfaces made of different materials and thus exhibiting different refractive-index spectra. So, when the plurality of spectro-polarimetric measurements have been taken, they are partitioned into sets in accordance with the material from which the radiation they measured was reflected. This can be done, for example, by employing a prior-art spectral-intensity (Stokes parameter I) analysis to group together measurements whose spectral "fingerprints" are similar. For each measurement set, this analysis will also reveal wavelength ranges in which resonances to be characterized are located.

The basic inference technique begins conceptually with Equation (14), which expresses the polarimetric-measurement values in terms of, among other things, the Fresnel reflectance factors $a_{\theta,\lambda}$, $b_{\theta,\lambda}$, $c_{\theta,\lambda}$, and $d_{\theta,\lambda}$. Those factors in turn are related by Equation (4) to the index of refraction $n_\lambda$ and thereby to the resonance's width, location-frequency, and strength parameters discussed above in connection with Equation (19). Substituting those relationships into Equation (14) relates the measurements to the desired resonance parameters. Of course, those relationships include a large number of unknowns, but measurements can be taken at enough wavelengths in each direction to over-constrain the problem and thus make it amenable to solution by (non-linear) regression.

Still, thus determining the resonance parameters is potentially onerous computationally, so most embodiments of the invention that thus make blind inferences of the refractive-index spectrum from spectro-polarimetric measurements are likely to employ some computation-reduction expedients in doing so. One expedient that all approaches will need to employ, for instance, is to assume some limit on how many resonances have any significant effect on the spectrum near the resonance of interest. As will be indicated below, for example, I have performed successful simulations that assume only one resonance above the resonance of interest and only one below it.

Another expedient is to choose measurements in such a way as to simplify the inference computation. Inspection of Equation (14)'s expressions for $Q'_r$ and $U_r'$ reveals that the former is proportional to $c_{\theta,\lambda}$ when $2(\gamma-\phi)=\pi\pm\pi/2$, whereas the latter is proportional to $c_{\theta,\lambda}$ when $2(\gamma-\phi)=0$ or $\pi$. This suggests restricting attention to measurements for which one or the other of those conditions apply. Of course, that requires identifying such measurements. As was observed above, $\gamma$ is known from the observation direction $(\alpha,\beta)$, so only rotation angle $\phi$ must be determined.

For non-metals, this can be achieved by employing Equation (17) for spectral samples falling within "normal dispersion" [Wooten1972, Ward1994] spectral regions, i.e., by employing samples from wavelength bands that are not near resonance features. This is valid for non-metals because Fresnel reflectance factor $c_{\theta,\lambda}$ is near zero in such regions for all but near-grazing (greater than 80 degrees) incidence angles $\theta$.

With the rotation angle $\phi$ thus known for each direction in a measurement set, attention can be restricted to measurements for which $2(\gamma-\phi)$ is close to 0 or multiples of 90 degrees. These are the measurements from which the resonance parameters can be inferred expediently. We infer those parameters by employing global non-linear regression ("GNLR") to minimize the following quadratic-error sum:

$$z[\{\{v_0, \Gamma_0, c_0\}, \{v_a, \Gamma_a, c_a\}, \{v_b, \Gamma_b, c_b\}\}, \quad (20)$$
$$\{\{k_1, \theta_1\}, \{k_2, \theta_2\}...\{k_i, \theta_i\}\}] =$$
$$\sum_i \sum_v \left( x_{i,v} - k_i \cdot c_{\theta,\lambda} \left[ \theta_i, \sqrt{1 + \sum_j^{0,a,b} \frac{c_j v_j^2}{v_j^2 - v^2 - i\Gamma_j v_j v}} \right] \right)^2$$

Here z is the sum, and its arguments are the unknowns to be varied in order to minimize z. The quantity $x_{i,\lambda}$ is the Stokes radiance component $Q'_r$ or $U_r'$ that, because of the above-mentioned judicious measurement selection, is proportional to $c_{\theta,\lambda}$, while index i represents a given direction and index v represents (by the corresponding frequency) the wavelength band at which the measurement was taken. Unknown parameters $v_0$, $\Gamma_0$, and $c_0$ respectively refer to the location, width, and strength of the resonance being characterized: they are the parameters whose values the regression operation is being undertaken to determine. The refractive-index spectrum in that resonance's neighborhood is assumed to be otherwise affected by only two (possibly negligible-strength) resonances, one of which is characterized by (unknown) parameters $v_a$, $\Gamma_a$, and $c_a$, the other of which is characterized by (again, unknown) parameters $v_b$, $\Gamma_b$, and $c_b$. Although these six ancillary parameters are not suitable for independent use, their estimation is necessary to account for the behavior of resonance feature $\{v_0, \Gamma_0, c_0\}$ in its "wings" (i.e. at off-center wavelengths). The remaining unknown parameters $\{k_1, \theta_1\}, \{k_2, \theta_2\} \ldots \{k_i, \theta_i\}$ are nuisance parameters with regard to estimating the refractive-index spectrum $n_\lambda$. They represent a particular remote-surface measurement's unknown incidence angle $\theta_i$ and radiance scale $k_i$.

An example of a suitable GNLR routine suitable for the above-described method is the Global Optimization package for Mathematica from Loehle Enterprises.

The formulation of these individual error terms of Equation (20) bears further discussion. Although Equation (14) shows that the Fresnel reflectance factors are multiplied by unknown nuisance factors (e.g. surface roughness $k_{\theta,\lambda}$, atmospheric transmittance $\tau_\lambda$, and illumination terms), the spectral variation in such nuisance factors typically either is known (in the case of transmittance and illumination) or varies slowly (in the case of surface roughness) over the resonance feature's spectral range. The resultant spectral bias of $Q_r'$ and $U_r'$ can therefore be removed by pre-processing. In some applications, one may know that $b_{\theta,\lambda}(I_{i,\lambda}-L_\lambda)$ dominates $a_{\theta,\lambda}Q_{i,\lambda}$ (cf. Equation (14)). If so, not only Fresnel reflectance factor $c_{\theta,\lambda}$ but also factor $b_{\theta,\lambda}$ can be used in constructing Equation (20)'s error terms.

Indeed, there are cases in which it is preferable to base the error terms on $b_{\theta,\lambda}$. Specifically, the polarized-illumination term, $U_{i,\lambda}$, that "drives" $c_{\theta,\lambda}$ may be negligible. When that happens, $c_{\theta,\lambda}$ may not be manifest with enough SNR in $Q_r'$ and $U_r'$. This low-SNR situation can readily be detected by applying an SNR criterion to whichever measured component, $Q_r'$ or $U_r'$, would, for the selected measurement direction, be used in Equation (20) as $x_{i,v}$ when the modeled reflectance factor is, as that equation indicates, $c_{\theta,\lambda}$. When that situation is detected, it is often possible instead to use the other measured component ($Q_r'$ or $U_r'$) as $x_{i,v}$ and use $b_{\theta,\lambda}$ in place of $c_{\theta,\lambda}$ as the modeled reflectance factor with which the measured component is compared. This is true because $Q_{i,\lambda}$ is often negligible when $U_{i,\lambda}$ is, so Equation (14)'s $b_{\theta,\lambda}(I_{i,\lambda}-L_\lambda)$ term usually dominates its $a_{\theta,\lambda}Q_{i,\lambda}$ term in such a situation.

The GNLR operation's performance will benefit from imposing appropriate bounds on the unknown parameters' allowable values. Bounds for the unknown scale factor $k_i$ for each measurement can be estimated by examining the ratio of $Q_r'$ (or $U_r'$) to $c_{\theta,\lambda}$ (or $b_{\theta,\lambda}$). The spectral location $v_0$ and relative width $\Gamma_0$ of the resonance feature can be readily estimated from the measurement data. The strength factor $c_0$ typically ranges between 0 and 1. Search bounds on spectral locations $v_a$ and $v_b$ should be set to span one to two octaves above and below $v_0$.

Although the GNLR approach to refractive-index-spectrum estimation can in principle be performed successfully by using a single surface (spectral) measurement, doing so would likely demand too high a sensor SNR. With only two measurements, though, I have simulated a successful spectrum determination with a sensor whose SNR is 200:1. Specifically, the estimation was performed against a Lorentzian resonance for $c_{74,\lambda}$ and reproduced separately for $b_{\theta,\lambda}$ by taking thirty-two spectral samples across a neighborhood of about three times the resonance width in each of two directions (e.g., one at $\theta=30$ degrees and the other at $\theta=60$ degrees—but with these angles taken as unknowns).

Successful blind estimation of $n_\lambda$ requires some difference among the measured radiation's incidence angles, and it improves up to a point as the number of measurements increases.

Indication of Surface Multiplicity

In the discussion so far, we have tacitly assumed that the surface being measured has only a single orientation. Of course, real surfaces often have corners, and the field of view employed in a given measurement may straddle a corner. Since a plurality of measurements from contiguous fields of view are used to create a composite image in many applications, we refer to a measurement's field of view as a picture element, or pixel.

Equations (16) and (17) pertain to the inference of angle $\phi$ under Case 2-regime conditions. If the sensor pixel subtends a singly oriented surface element, these equations indicate that the retrieved value for φ is independent of spectral-sample location λ (not-withstanding random-noise deviations). But the sensor pixel may subtend multiple surfaces of differing orientations. If so, a resultant spectral variation in retrieved φ values can provide a cue to this situation. Equation (21) re-expresses Equation (17) from Equation (16) for the case of multiple subtended surfaces (each surface indexed by subscript "j"). Since, as FIGS. 8 and 9 illustrate, the Fresnel reflectance factors $b_{\theta,\lambda}$ and $a_{\theta,\lambda}$ vary in magnitude with $\theta_j$ and λ, Equation (21) implies that the retrieved φ will spectrally vary between limit values. These limit values can be indicative of the extent of spread among the surface orientations $\theta_j$.

$$\phi_\lambda = \gamma + \frac{1}{2}\mathrm{ArcTan}\left[\frac{\sum_j -\mathrm{Sin}2(\gamma - \phi_j)\left[b_{\theta_j,\lambda}(I_{i,\lambda} - L_\lambda) + a_{\theta_j,\lambda}Q_{i,\lambda}\right]}{\sum_j -\mathrm{Cos}2(\gamma - \phi_j)\left[b_{\theta_j,\lambda}(I_{i,\lambda} - L_\lambda) + a_{\theta_j,\lambda}Q_{i,\lambda}\right]}\right] + \left\{\begin{array}{c}0\\90\end{array}\right\} \quad (21)$$

This cue may instigate an adaptive refinement in the pixel field of view in an attempt to subtend more-uniformly oriented surface segments. On the other hand, the cue can be used simply to flag such measurement pixels as being unreliable.

Preferred and Alternative Embodiments

Although the illustrated embodiment shows that the invention can be implemented effectively by measuring mere handful of well-chosen spectral bands about a known resonance, more-extensive measuring may be preferable for some applications. A hyperspectral sensor providing fine spectral resolution in numerous bands could be used to afford agility of application against various material types, each exhibiting resonances at varying spectral positions and widths.

Despite this flexibility, most practical implementations will probably employ a hyperspectral polarimeter operating in a only a single range, spanning on the order of, say, an octave in the non-solar thermal infrared range (e.g., 8–14 micrometers). There are several reasons for this choice.

First, at spatial scales commensurate with man-made objects, both natural and indoor environmental illumination is generally only weakly polarized (e.g., DoP<5%). In this low-DoP illumination regime, the subject invention offers good performance across the entire range of surface-incident AoP and angles of incidence θ. Second, man-made objects, particularly polymers, exhibit an abundance of resonance features in this spectral regime. Third, surfaces appear smoother and thus more glossy and Fresnel-like in this band than in the visible band. This maximizes the polarization signal level. Fourth, the absence of the intense solar point source eliminates potential confusion between, on the one hand, polarized radiance generated by low-intensity environmental radiance reflected at the specular lobe peak, and on the other, high-intensity solar radiance reflected well off the lobe peak. Finally, the illumination's spectral variability is favorably predictable. This is particularly helpful when a resonance used in Case 2 to infer θ is broad enough spectrally that the illumination intensity cannot be assumed to be spectrally constant.

Factors militating against the thermal infrared are typically the much higher sensor costs (relative to the visible band), and the potential 90-degree ambiguity in φ that results from ambiguity as to whether it is emission or reflection that dominates. Nevertheless, this ambiguity can be dealt with in an application-specific manner. For instance, the dominance may be presumed to be based on the relative temperatures of the surfaces with respect to the environmental illumination (e.g., warm bodies reflecting the cold sky), or inferred from the Planck spectral shaping of the measured intensity.

Still, the invention's extraction of useful topometric information from optical spectro-polarimetric radiance measurements is in principle indifferent to the particular type of spectro-polarimetric sensor employed. For example, the sensor can operate in other spectral regions, e.g., visible, near infrared, other thermal infrared, etc. And the sensor need not be an imaging device; for instance, it could be a spot scanner. Also, the sensor need not be passive; for instance, it could employ a spectrally tunable active source. The sensor may employ either time-sequential or time-simultaneous polarimetry, so long as measurement registration error is controlled to within the desired SNR.

All such alternatives can be employed to implement the present invention's teaching of topometrically exploiting the fact that the spectral patterns exhibited by Fresnel reflectance factors across a Lorentzian or plasma resonance change characteristically with incidence angle. And they can be used for a variety of purposes. One application is 3D object geometry capture or 3D scanning. For this purpose, it may be used alone or, say, to augment existing laser-based spot triangulation scanners so that glossy surfaces can be dealt with successfully. It can be used for technical/engineering surface topometry. An example is spectro-ellipometry for combined epitaxial deposition-depth and orientation monitoring. Sports-diagnostic videography is another application; it could be used, for example to record golf-club-face orientation during a golf swing. It can be used to monitor distant facilities remotely to determine whether windows or doors are open. Similar inspection of distant roadway signs or transportation navigation aids for misorientation is another use, as is determining plant-canopy architecture for agricultural and earth-resource monitoring.

So the present invention can be used in a wide range of applications and is a significant advance in the art.

What is claimed is:

1. A method for measuring the three-dimensional orientation of a remote surface, which method comprises:
    A) at each of plurality of wavelengths in a resonance neighborhood in which a remote surface's index of refraction exhibits a resonance, measuring the polarization state of the radiation received from the surface;
    B) inferring the surface's three-dimensional orientation from the thereby-measured spectral behavior of the radiation's polarization state by employing a mathematical model of surface radiation-spectrum modulation that includes the dependence on angle of incidence of Fresnel reflectance as a function of wavelength in the neighborhood of a refractive-index resonance and in which any component of the received radiation resulting from reflection from the surface is assumed to have resulted from reflection of incident radiation whose elliptical polarization is negligible; and
    C) generating an orientation signal representative of the orientation thereby inferred.

2. A method as defined in claim 1 that further includes inferring the location of the resonance neighborhood from spectral measurements of radiation received from the surface.

3. A method as defined in claim 1 that further includes inferring the dependence on angle of incidence of Fresnel reflectance as a function of wavelength in the neighborhood of a refractive-index resonance from the polarization state of radiation received from the surface.

4. A method as defined in claim 3 wherein the dependence on angle of incidence of Fresnel reflectance as a function of wavelength in the neighborhood of a refractive-index resonance is inferred by:
- A) making a plurality of measurements of the polarization state of radiation received from the surface;
- B) computing strength, width, and wavelength parameters of the refractive-index resonance by employing global nonlinear regression analysis to find the values thereof that minimize the error between the measurements and predictions made by a mathematical model of surface radiation-spectrum modulation that predicts values of the measurements from refractive-index-resonance strength, width, and wavelength parameters; and
- C) computing the Fresnel reflectance from the strength, width, and wavelength parameters thus computed.

5. A method as defined in claim 1 wherein:
- A) the method further includes:
  - i) for each of a plurality of test incidence angles, computing a set, associated with that test incidence angle, of test rotation angles by computing, for each of a plurality of the wavelengths, a test rotation angle by employing the respective Fresnel reflectance factors implied in accordance with the model by that incidence angle; and
  - ii) determining whether the set of test rotation angles associated with any of the test incidence angles meets a consistency criterion; and
- B) the rotation angle represented by the orientation signal is determined from a set of test rotation angles thus computed, and the incidence angle represented by the orientation signal is the test incidence angle with which that set of rotation angles is associated, only if that set of rotation angles was thereby determined to meet the consistency criterion.

6. A method as defined in claim 5 wherein:
- A) the rotation angle represented by the orientation signal is determined from the most-consistent of the sets of test rotation angles if that set of test rotation angles meets the consistency criterion; and
- B) the incidence angle represented by the orientation signal is the test incidence angle with which that set of test rotation angles is associated.

7. A method as defined in claim 5 wherein, if none of the sets of test rotation angles meets the consistency criterion:
- A) the method further includes:
  - i) computing from the polarization-state measurements the value of a feature vector whose components are a function of at least one Fresnel-reflectance-factor-dependent component of the polarization-state measurement at respective wavelengths; and
  - ii) employing a function that relates incidence angle to feature-vector value to determine an incidence angle from that value; and
- B) the incidence angle represented by the orientation signal is the incidence angle thereby determined.

8. A method as defined in claim 7 wherein:
- A) the method further includes employing the mathematical model under the assumption of non-obliquely polarized illumination to compute a second set of test rotation angles from measurements taken at a plurality of wavelengths;
- B) if the second set of test rotation angles meets a consistency criterion or the incidence angle determined is not less than a maximum incidence-angle value:
  - i) the method includes determining a rotation angle from the second set of test rotation angles; and
  - ii) the rotation angle represented by the orientation signal is the rotation angle thereby determined; and
- C) otherwise:
  - i) the method includes employing the mathematical model without the assumption of non-obliquely polarized illumination to compute a rotation angle from the measurements and the determined incidence angle; and
  - ii) the rotation angle represented by the orientation signal is the rotation angle thereby determined.

9. A method as defined in claim 1 wherein:
- A) the method further includes:
  - i) computing from the polarization-state measurements the value of a feature vector whose components are a function of at least one Fresnel-reflectance-factor-dependent component of the polarization-state measurement at respective wavelengths; and
  - ii) employing a function that relates incidence angle to feature-vector value to determine an incidence angle from that value; and
- B) the incidence angle represented by the orientation signal is the incidence angle thereby determined.

10. A method as defined in claim 9 wherein:
- A) the orientation signal represents the incidence angle and a rotation angle; and
- B) the rotation angle represented by the orientation signal is computed by assuming non-obliquely polarized illumination.

11. An apparatus for measuring the three-dimensional orientation of a remote surface, which apparatus comprises:
- A) a polarization sensor that, at each of a plurality of wavelengths in a resonance neighborhood in which a remote surface's index of refraction exhibits a resonance, measures the polarization state of the radiation received from the surface and generates a polarization-state output indicative thereof; and
- B) orientation-determination circuitry that:
  - i) computes the surface's three-dimensional orientation from the thereby-measured spectral behavior of the radiation's polarization state indicated by the polarization-state output by employing a mathematical model of surface radiation-spectrum modulation that includes the dependence on angle of incidence of Fresnel reflectance as a function of wavelength in the neighborhood of a refractive-index resonance and in which any component of the received radiation resulting from reflection from the surface is assumed to have resulted from reflection of incident radiation whose elliptical polarization is negligible; and
  - ii) generates an orientation signal representative of the orientation thereby computed.

12. An apparatus as defined in claim 11 wherein the orientation-determination circuitry additionally infers the location of the resonance neighborhood from spectral measurements of radiation received from the surface.

13. An apparatus as defined in claim 11 wherein the orientation-determination circuitry additionally infers the dependence on angle of incidence of Fresnel reflectance as a function of wavelength in the neighborhood of a refractive-index resonance from the polarization state of radiation received from the surface.

14. An apparatus as defined in claim 13 wherein the dependence on angle of incidence of Fresnel reflectance as a function of wavelength in the neighborhood of a refractive-index resonance is inferred by:
  A) making a plurality of measurements of the polarization state of radiation received from the surface;
  B) computing strength, width, and wavelength parameters of the refractive-index resonance by employing global nonlinear regression analysis to find the values thereof that minimize the error between the measurements and predictions made by a mathematical model of surface radiation-spectrum modulation that predicts values of the measurements from refractive-index-resonance strength, width, and wavelength parameters; and
  C) computing the Fresnel reflectance from the strength, width, and wavelength parameters thus computed.

15. An apparatus as defined in claim 11 wherein:
  A) the orientation-determination circuitry additionally:
    i) for each of a plurality of test incidence angles, computes a set, associated with that test incidence angle, of test rotation angles by computing, for each of a plurality of the wavelengths, a test rotation angle by employing the respective Fresnel reflectance factors implied in accordance with the model by that incidence angle; and
    ii) determines whether the set of test rotation angles associated with any of the test incidence angles meets a consistency criterion; and
  B) the rotation angle represented by the orientation signal is determined from a set of test rotation angles thus computed, and the incidence angle represented by the orientation signal is the test incidence angle with which that set of rotation angles is associated, only if that set of rotation angles was thereby determined to meet the consistency criterion.

16. An apparatus as defined in claim 15 wherein:
  A) the rotation angle represented by the orientation signal is determined from the most-consistent of the sets of test rotation angles if that set of test rotation angles meets the consistency criterion; and
  B) the incidence angle represented by the orientation signal is the test incidence angle with which that set of test rotation angles is associated.

17. An apparatus as defined in claim 15 wherein, if none of the sets of test rotation angles meets the consistency criterion:
  A) the orientation-determination circuitry:
    i) computes from the polarization-state measurements the value of a feature vector whose components are a function of at least one Fresnel-reflectance-factor-dependent component of the polarization-state measurement at respective wavelengths; and
    ii) employs a function that relates incidence angle to feature-vector value to determine an incidence angle from that value; and
  B) the incidence angle represented by the orientation signal is the incidence angle thereby determined.

18. An apparatus as defined in claim 17 wherein:
  A) the orientation-determination circuitry employs the mathematical model under the assumption of non-obliquely polarized illumination to compute a second set of test rotation angles from measurements taken at a plurality of wavelengths;
  B) if the second set of test rotation angles meets a consistency criterion or the incidence angle determined is not less than a maximum incidence-angle value:
    i) the orientation-determination circuitry determines a rotation angle from the second set of test rotation angles; and
    ii) the rotation angle represented by the orientation signal is the rotation angle thereby determined; and
  C) otherwise:
    i) the orientation-determination circuitry employs the mathematical model without the assumption of non-obliquely polarized illumination to compute a rotation angle from the measurements and the determined incidence angle; and
    ii) the rotation angle represented by the orientation signal is the rotation angle thereby determined.

19. An apparatus as defined in claim 11 wherein:
  A) the orientation-determination circuitry further:
    i) computes from the polarization-state measurements the value of a feature vector whose components are a function of at least one Fresnel-reflectance-factor-dependent component of the polarization-state measurement at respective wavelengths; and
    ii) employing a function that relates incidence angle to feature-vector value to determine an incidence angle from that value; and
  B) the incidence angle represented by the orientation signal is the incidence angle thereby determined.

20. An apparatus as defined in claim 19 wherein:
  A) the orientation signal represents the incidence angle and a rotation angle; and
  B) the rotation angle represented by the orientation signal is computed by assuming non-obliquely polarized illumination.

* * * * *